United States Patent
Nitzan et al.

(10) Patent No.: US 9,980,815 B2
(45) Date of Patent: May 29, 2018

(54) DEVICES FOR REDUCING LEFT ATRIAL PRESSURE, AND METHODS OF MAKING AND USING SAME

(71) Applicant: V-Wave Ltd., Caesarea (IL)

(72) Inventors: Yaacov Nitzan, Hertzelia (IL); Menashe Yacoby, Ramat Gan (IL)

(73) Assignee: V-Wave Ltd., Caesarea (IL)

( * ) Notice: Subject to any disclaimer, the term of this patent is extended or adjusted under 35 U.S.C. 154(b) by 119 days.

(21) Appl. No.: 14/712,801

(22) Filed: May 14, 2015

(65) Prior Publication Data
US 2015/0245908 A1 Sep. 3, 2015

Related U.S. Application Data

(60) Division of application No. 13/193,335, filed on Jul. 28, 2011, now Pat. No. 9,034,034, which is a
(Continued)

(51) Int. Cl.
*A61F 2/82* (2013.01)
*A61F 2/24* (2006.01)
*A61B 17/00* (2006.01)

(52) U.S. Cl.
CPC .......... *A61F 2/2412* (2013.01); *A61F 2/2415* (2013.01); *A61F 2/2418* (2013.01);
(Continued)

(58) Field of Classification Search
CPC ....................................................... A61F 2/82
See application file for complete search history.

(56) References Cited

U.S. PATENT DOCUMENTS

| | | |
|---|---|---|
| 3,874,388 A | 4/1975 | King et al. |
| 3,952,334 A | 4/1976 | Bokros et al. |

(Continued)

FOREIGN PATENT DOCUMENTS

| | | |
|---|---|---|
| FR | 2827153 | 1/2003 |
| WO | WO-99/60941 A1 | 12/1999 |

(Continued)

OTHER PUBLICATIONS

Braunwald, Heart Disease, Chapter 6, p. 186.
(Continued)

*Primary Examiner* — Matthew Schall
(74) *Attorney, Agent, or Firm* — Foley & Lardner LLP; Christopher C. Bolten; Nicola A. Pisano

(57) ABSTRACT

A device for regulating blood pressure between a patient's left atrium and right atrium comprises an hourglass-shaped stent comprising a neck region and first and second flared end regions, the neck region disposed between the first and second end regions and configured to engage the fossa ovalis of the patient's atrial septum; and a one-way tissue valve coupled to the first flared end region and configured to shunt blood from the left atrium to the right atrium when blood pressure in the left atrium exceeds blood pressure in the right atrium. The inventive devices may reduce left atrial pressure and left ventricular end diastolic pressure, and may increase cardiac output, increase ejection fraction, relieve pulmonary congestion, and lower pulmonary artery pressure, among other benefits. The inventive devices may be used, for example, to treat subjects having heart failure, pulmonary congestion, or myocardial infarction, among other pathologies.

34 Claims, 19 Drawing Sheets

Related U.S. Application Data continuation-in-part of application No. PCT/IL2010/000354, filed on May 4, 2010.

(60) Provisional application No. 61/425,792, filed on May 4, 2010, provisional application No. 61/175,073, filed on May 4, 2009, provisional application No. 61/240,667, filed on Sep. 9, 2009.

(52) U.S. Cl.
CPC .......... *A61B 2017/00575* (2013.01); *A61B 2017/00592* (2013.01); *A61B 2017/00597* (2013.01); *A61B 2017/00606* (2013.01); *A61B 2017/00623* (2013.01); *A61F 2220/005* (2013.01); *A61F 2220/0058* (2013.01); *A61F 2220/0075* (2013.01); *A61F 2230/001* (2013.01); *A61F 2230/005* (2013.01); *A61F 2230/0078* (2013.01)

(56) References Cited

U.S. PATENT DOCUMENTS

| | | |
|---|---|---|
| 4,601,309 A | 7/1986 | Chang |
| 4,662,355 A | 5/1987 | Pieronne et al. |
| 4,705,507 A | 11/1987 | Boyles |
| 4,836,204 A | 6/1989 | Landymore et al. |
| 4,979,955 A | 12/1990 | Smith |
| 4,995,857 A | 2/1991 | Arnold |
| 5,186,431 A | 2/1993 | Tamari |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,556,386 A | 9/1996 | Todd |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,916,193 A | 6/1999 | Stevens et al. |
| 5,941,850 A | 8/1999 | Shah et al. |
| 5,957,949 A | 9/1999 | Leonhardt et al. |
| 6,039,759 A | 3/2000 | Carpentier et al. |
| 6,117,159 A | 9/2000 | Huebsch et al. |
| 6,120,534 A | 9/2000 | Ruiz |
| 6,126,686 A | 10/2000 | Badylak et al. |
| 6,165,188 A | 12/2000 | Saadat et al. |
| 6,210,318 B1 | 4/2001 | Lederman |
| 6,217,541 B1 | 4/2001 | Yu |
| 6,242,762 B1 | 6/2001 | Brown et al. |
| 6,254,564 B1 | 7/2001 | Wilk et al. |
| 6,260,552 B1 | 7/2001 | Mortier et al. |
| 6,270,526 B1 | 8/2001 | Cox |
| 6,277,078 B1 | 8/2001 | Porat et al. |
| 6,302,892 B1 | 10/2001 | Wilk |
| 6,328,699 B1 | 12/2001 | Eigler et al. |
| 6,344,022 B1 | 2/2002 | Jarvik |
| 6,358,277 B1 | 3/2002 | Duran |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,491,705 B2 | 12/2002 | Gifford et al. |
| 6,527,698 B1 | 3/2003 | Kung et al. |
| 6,544,208 B2 | 4/2003 | Ethier et al. |
| 6,562,066 B1 | 5/2003 | Martin |
| 6,572,652 B2 | 6/2003 | Shaknovich |
| 6,589,198 B1 | 7/2003 | Soltanpour et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 7,001,409 B2 | 2/2006 | Amplatz |
| 7,149,587 B2 | 12/2006 | Wardle et al. |
| 7,294,115 B1 | 11/2007 | Wilk |
| 7,794,473 B2 | 9/2010 | Tessmer et al. |
| 7,988,724 B2 | 8/2011 | Salahieh et al. |
| 8,016,877 B2 | 9/2011 | Seguin et al. |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,147,545 B2 | 4/2012 | Avior |
| 8,157,860 B2 | 4/2012 | McNamara et al. |
| 8,235,916 B2 | 8/2012 | Whiting et al. |
| 8,235,933 B2 | 8/2012 | Keren et al. |
| 8,246,677 B2 | 8/2012 | Ryan |
| 8,303,511 B2 | 11/2012 | Eigler et al. |
| 8,328,751 B2 | 12/2012 | Keren et al. |
| 8,348,996 B2 | 1/2013 | Tuval et al. |
| 8,398,708 B2 | 3/2013 | Meiri et al. |
| 8,460,366 B2 | 6/2013 | Rowe |
| 8,579,966 B2 | 11/2013 | Seguin et al. |
| 8,597,225 B2 | 12/2013 | Kapadia |
| 8,696,611 B2 | 4/2014 | Nitzan et al. |
| 9,034,034 B2 | 5/2015 | Nitzan et al. |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2004/0010219 A1 | 1/2004 | McCusker et al. |
| 2004/0016514 A1 | 1/2004 | Nien |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0033351 A1 | 2/2005 | Newton |
| 2005/0065589 A1 | 3/2005 | Schneider et al. |
| 2005/0137682 A1 | 6/2005 | Justino |
| 2005/0148925 A1 | 7/2005 | Rottenberg et al. |
| 2005/0165344 A1 | 7/2005 | Dobak, III |
| 2005/0182486 A1 | 8/2005 | Gabbay |
| 2005/0283231 A1 | 12/2005 | Haug et al. |
| 2006/0025857 A1 | 2/2006 | Bergheim et al. |
| 2006/0111660 A1 | 5/2006 | Wolf et al. |
| 2006/0116710 A1 | 6/2006 | Corcoran et al. |
| 2006/0122647 A1 | 6/2006 | Callaghan et al. |
| 2006/0167541 A1 | 7/2006 | Lattouf |
| 2006/0212110 A1 | 9/2006 | Osborne et al. |
| 2006/0282157 A1 | 12/2006 | Hill et al. |
| 2007/0010852 A1 | 1/2007 | Blaeser et al. |

(56) References Cited

U.S. PATENT DOCUMENTS

| | | |
|---|---|---|
| 2007/0043435 A1 | 2/2007 | Seguin et al. |
| 2007/0213813 A1 | 9/2007 | Von Segesser et al. |
| 2007/0282157 A1 | 12/2007 | Rottenberg et al. |
| 2007/0299384 A1 | 12/2007 | Faul et al. |
| 2008/0086205 A1 | 4/2008 | Gordy et al. |
| 2008/0262602 A1 | 10/2008 | Wilk et al. |
| 2009/0054976 A1 | 2/2009 | Tuval et al. |
| 2009/0125104 A1 | 5/2009 | Hoffman |
| 2009/0276040 A1 | 11/2009 | Rowe et al. |
| 2010/0004740 A1 | 1/2010 | Seguin et al. |
| 2010/0057192 A1 | 3/2010 | Celermajer |
| 2010/0249909 A1* | 9/2010 | McNamara ........ A61B 17/0057 623/1.26 |
| 2010/0249910 A1 | 9/2010 | McNamara et al. |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0306916 A1 | 12/2011 | Nitzan et al. |
| 2012/0071918 A1 | 3/2012 | Amin et al. |
| 2012/0165928 A1 | 6/2012 | Nitzan et al. |
| 2012/0271398 A1 | 10/2012 | Essinger et al. |
| 2013/0030521 A1 | 1/2013 | Nitzan et al. |
| 2013/0197423 A1 | 8/2013 | Keren et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0213959 A1 | 7/2014 | Nitzan et al. |
| 2014/0350565 A1 | 11/2014 | Yacoby et al. |
| 2015/0039084 A1 | 2/2015 | Levi et al. |
| 2015/0245908 A1 | 9/2015 | Nitzan et al. |

FOREIGN PATENT DOCUMENTS

| | | | |
|---|---|---|---|
| WO | WO-2005/027752 A1 | 3/2005 | |
| WO | WO-2005/074367 A1 | 8/2005 | |
| WO | WO-2006/127765 A1 | 11/2006 | |
| WO | WO-2007/083288 A2 | 7/2007 | |
| WO | WO-2008/055301 A1 | 5/2008 | |
| WO | WO-2009/029261 A1 | 3/2009 | |
| WO | WO-2010/128501 A1 | 11/2010 | |

OTHER PUBLICATIONS

Bridges, et al., The Society of Thoracic Surgeons Practice Guideline Series: Transmyocardial Laser Revascularization, Ann Thorac Surg., 77:1494-1502 (2004).

Extended EP Search Report dated Sep. 19, 2016 in EP Patent Application Serial No. 16170281.6.

Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).

Park Blade Septostomy Catheter Instructions for Use, Cook Medical, 28 pages, Oct. 2015.

Park, et al., Blade Atrial Septostomy: Collaborative Study, Circulation, 66(2):258-266 (1982).

Roven et al., "Effect of Compromising Right Ventricular Function in Left Ventricular Failure by Means of Interatrial and Other Shunts," American Journal Cardiology, 24:209-219 (1969).

Salehian et al., Improvements in Cardiac Form and Function After Transcatheter Closure of Secundum Atrial Septal Defects, Journal of the American College of Cardiology, 45(4):499-504 (2005).

Schmitto et al., Chronic heart failure induced by multiple sequential coronary microembolization in sheep, The International Journal of Artificial Organs, 31(4):348-353 (2008).

Trainor et al., Comparative Pathology of an Implantable Left Atrial Pressure Sensor, ASAIO Journal, Clinical Cardiovascular/Cardiopulmonary Bypass, 59(5):486-92 (2013).

Ando et al., "Left vetricular decompression through a patent foramen ovale in a patient with hypertrophic cardiomyopathy: A case report," Cardiovascular Ultrasound, (2004), 2:1-7.

Article 34 Amendments dated May 28, 2013 in related International PCT Patent Appl No. PCT/IB2012/001859.

Article 34 Amendments dated Nov. 27, 2012, as filed in related Int'l PCT Application No. PCT/IS2011/000958.

Bristow et al., "Improvement in cardiac myocyte function by biological effects of medical therapy: Anew concept in the treatment of heart failure," European Heart Journal, (1995), 16(Suppl.F):20-31.

Case et al., "Relief of High Left-Atrial Pressure in Left-Ventricular Failure," Lancet, (Oct. 17, 1964), pp. 841-842.

Coats et al., "Controlled trial of physical training in chronic heart failure: Exercise preformance, hemodynamics, ventilation, and autonomic function," Circulation, (1992), 85:2119-2131.

Davies et al., "Reduced contraction and altered frequency response of isolated ventricular myocytes from patients with heart failure," Circulation, (1995), 92:2540-2549.

Ennezat et al., "An unusual case of low-flow, low gradient severe aortic stenosis: Left-to-right shunt due to atrial septal defect," Cardiology, (2009), 113(2):146-148.

Ewert et al., "Acute left heart failure after interventional occlusion of an atrial septal defect," Z. Kardiol., (May 2001), 90(5):362-366.

Ewert et al., "Masked left ventricular restriction in elderly patients with atrial septal defects: A contraindication for closure?" Catheterization and Cardiovascular Interventions, (2001), 52:177-180.

Extended European Search Report dated Jan. 8, 2015 in EP Patent Appl No. 10772089.8.

Geiran et al., "Changes in cardiac dynamics by opening an interventricular shunt in dogs," J. Surg. Res., (Jan. 1990), 48(1):6-12.

Gelernter-Yaniv et al., "Transcatheter closure of left-to-right interatrial shunts to resolve hypoxemia," Congenit. Heart Dis., (Jan. 2008), 31(1):47-53.

Gewillig et al., "Creation with a stent of an unrestrictive lasting atrial communication," Cardio. Young, (2002), 12(4):404-407.

International Preliminary Report on Patentability dated Nov. 14, 2013 in related International PCT Patent Appl No. PCT/IB2012/001859.

International Search Report for PCT/IL2005/000131 dated Apr. 7, 2008, (3 pages).

International Search Report for PCT/IL2010/000354 dated Aug. 25, 2010 (1 pg).

Int'l Preliminary Report on Patentability dated Mar. 5, 2013, in related Int'l PCT Patent Appl No. PCT/IL2011/000958.

ISR & Written Opinion dated Feb. 16, 2015 in Int'l PCT Patent Appl Serial No. PCT/IB2014/001771.

Kramer et al., "Controlled study of captopril in chronic heart failure: A rest and exercise hemodynamic study," Circulation, (1983), 67(4):807-816.

Lai et al., "Bidirectional shunt through a residual atrial septal defect after percutaneous transvenous mitral commissurotomy," Cardiology, (1993), 83(3):205-207.

Lemmer et al., "Surgical implications of atrial septal defect complicating aortic balloon valvuloplasty," Ann. thorac. Surg., (Aug. 1989), 48(2):295-297.

Merriam-Webster "Definition of 'Chamber'," OnLine Dictionary 2004, Abstract.

Schubert et al., "Left ventricular conditioning in the elderly patient to prevent congestive heart failure after transcatheter closure of the atrial septal defect," Catheter Cardiovasc. Interv., (2005), 64(3):333-337.

Stormer et al., "Comparative study of in vitro flow characteristics between a human aortic valve and a designed aortic and six corresponding types of prosthetic heart valves," European Surgical Research, (1976), 8(2):117-131.

Stumper et al., "Modified technique of stent fenestration of the atrial septum," Heart, (2003), 89:1227-1230.

(56) References Cited

OTHER PUBLICATIONS

Zhou et al., "Unidirectional valve patch for repair of cardiac septal defects with pulmonary hypertension," Annals of Thoracic Surgeons, (1995), 60:1245-1249.

* cited by examiner

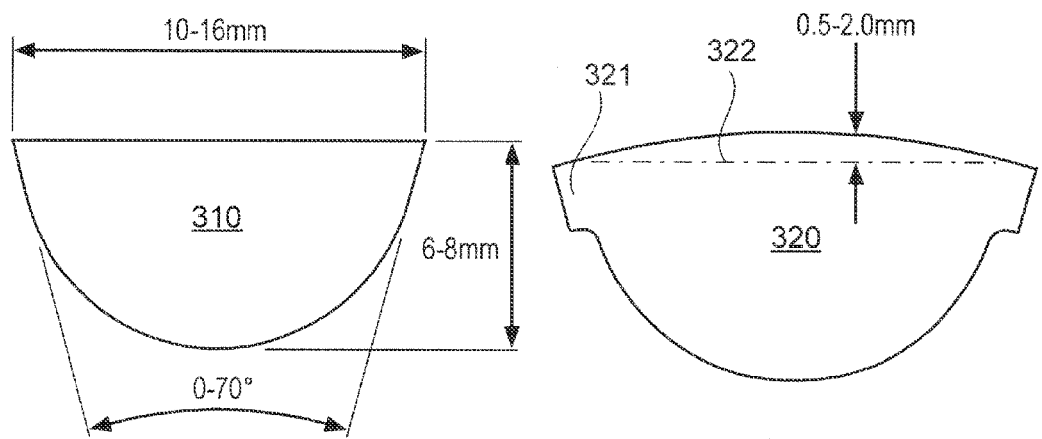
FIG. 3B
FIG. 3C
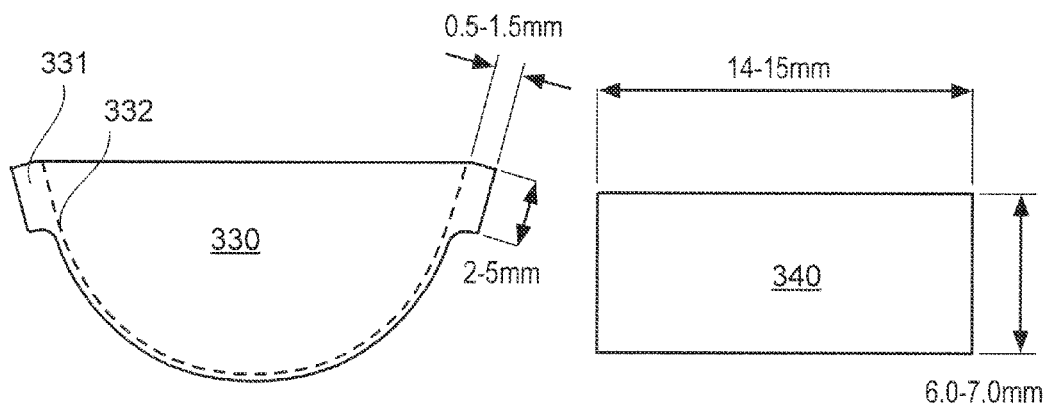
FIG. 3D
FIG. 3E

DEVICES FOR REDUCING LEFT ATRIAL PRESSURE, AND METHODS OF MAKING AND USING SAME

CROSS-REFERENCE TO RELATED APPLICATIONS

This application is a divisional under 35 U.S.C. § 120 of U.S. patent application Ser. No. 13/193,335, filed Jul. 28, 2011, now U.S. Pat. No. 9,034,034, which claims the benefit of U.S. Provisional Patent Application No. 61/425,792, filed Dec. 22, 2010 and entitled "Device and Method for Regulating Pressure in a Heart Chamber," the entire contents of which are incorporated by reference herein, and U.S. patent application Ser. No. 13/193,335 is also a continuation-in-part under 35 U.S.C. § 120 of International Patent Application No. PCT/IL2010/000354, filed May 4, 2010, which claims the benefit of U.S. Provisional Patent Application Nos. 61/175,073, filed May 4, 2009 and 61/240,667, filed Sep. 9, 2009, the entire contents of each of which are incorporated by reference herein.

FIELD OF THE INVENTION

This application generally relates to devices and methods for reducing left atrial pressure, particularly in subjects with heart pathologies such as congestive heart failure (CHF) or myocardial infarction (MI).

BACKGROUND OF THE INVENTION

Heart failure is the physiological state in which cardiac output is insufficient to meet the needs of the body and the lungs. CHF occurs when cardiac output is relatively low and the body becomes congested with fluid. There are many possible underlying causes of CHF, including myocardial infarction, coronary artery disease, valvular disease, and myocarditis. Chronic heart failure is associated with neurohormonal activation and alterations in autonomic control. Although these compensatory neurohormonal mechanisms provide valuable support for the heart under normal physiological circumstances, they also have a fundamental role in the development and subsequent progression of CHF. For example, one of the body's main compensatory mechanisms for reduced blood flow in CHF is to increase the amount of salt and water retained by the kidneys. Retaining salt and water, instead of excreting it into the urine, increases the volume of blood in the bloodstream and helps to maintain blood pressure. However, the larger volume of blood also stretches the heart muscle, enlarging the heart chambers, particularly the ventricles. At a certain amount of stretching, the heart's contractions become weakened, and the heart failure worsens. Another compensatory mechanism is vasoconstriction of the arterial system. This mechanism, like salt and water retention, raises the blood pressure to help maintain adequate perfusion.

In low ejection fraction (EF) heart failure, high pressures in the heart result from the body's attempt to maintain the high pressures needed for adequate peripheral perfusion. However, the heart weakens as a result of the high pressures, aggravating the disorder. Pressure in the left atrium may exceed 25 mmHg, at which stage, fluids from the blood flowing through the pulmonary circulatory system flow out of the interstitial spaces and into the alveoli, causing pulmonary edema and lung congestion.

Table 1 lists typical ranges of right atrial pressure (RAP), right ventricular pressure (RVP), left atrial pressure (LAP), left ventricular pressure (LVP), cardiac output (CO), and stroke volume (SV) for a normal heart and for a heart suffering from CHF. In a normal heart beating at around 70 beats/minute, the stroke volume needed to maintain normal cardiac output is about 60 to 100 milliliters. When the preload, after-load, and contractility of the heart are normal, the pressures required to achieve normal cardiac output are listed in Table 1. In a heart suffering from CHF, the hemodynamic parameters change (as shown in Table 1) to maximize peripheral perfusion.

TABLE 1

| Parameter | Normal Range | CHF Range |
|---|---|---|
| RAP (mmHg) | 2-6 | 6-15 |
| RVP (mmHg) | 15-25 | 20-40 |
| LAP (mmHg) | 6-12 | 15-30 |
| LVP (mmHg) | 6-120 | 20-220 |
| CO (liters/minute) | 4-8 | 2-6 |
| SV (milliliters/beat) | 60-100 | 30-80 |

CHF is generally classified as either systolic heart failure (SHF) or diastolic heart failure (DHF). In SHF, the pumping action of the heart is reduced or weakened. A common clinical measurement is the ejection fraction, which is a function of the blood ejected out of the left ventricle (stroke volume), divided by the maximum volume remaining in the left ventricle at the end of diastole or relaxation phase. A normal ejection fraction is greater than 50%. Systolic heart failure has a decreased ejection fraction of less than 50%. A patient with SHF may usually have a larger left ventricle because of a phenomenon called cardiac remodeling that occurs secondarily to the higher ventricular pressures.

In DHF, the heart generally contracts normally, with a normal ejection fraction, but is stiffer, or less compliant, than a healthy heart would be when relaxing and filling with blood. This stiffness may impede blood from filling the heart, and produce backup into the lungs, which may result in pulmonary venous hypertension and lung edema. DHF is more common in patients older than 75 years, especially in women with high blood pressure.

Both variants of CHF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure.

In more severe cases of CHF, assist devices such as mechanical pumps have been used to reduce the load on the heart by performing all or part of the pumping function normally done by the heart. Chronic left ventricular assist devices (LVAD), and cardiac transplantation, often are used as measures of last resort. However, such assist devices are typically intended to improve the pumping capacity of the heart, to increase cardiac output to levels compatible with normal life, and to sustain the patient until a donor heart for transplantation becomes available. Such mechanical devices enable propulsion of significant volumes of blood (liters/min), but are limited by a need for a power supply, relatively large pumps, and the risk of hemolysis, thrombus formation, and infection. Temporary assist devices, intra-aortic balloons, and pacing devices have also been used.

In addition to cardiac transplant, which is highly invasive and limited by the ability of donor hearts, surgical approaches such as dynamic cardiomyoplastic or the Batista partial left ventriculectomy may also be used in severe cases.

Various devices have been developed using stents or conduits to modify blood pressure and flow within a given vessel, or between chambers of the heart. For example, U.S. Pat. No. 6,120,534 to Ruiz is directed to an endoluminal stent for regulating the flow of fluids through a body vessel or organ, for example for regulating blood flow through the pulmonary artery to treat congenital heart defects. The stent may include an expandable mesh having lobed or conical portions joined by a constricted region, which limits flow through the stent. The mesh may comprise longitudinal struts connected by transverse sinusoidal or serpentine connecting members. Ruiz is silent on the treatment of CHF or the reduction of left atrial pressure.

U.S. Pat. No. 6,468,303 to Amplatz et al. discloses a collapsible medical device and associated method for shunting selected organs and vessels. Amplatz discloses that the device may be suitable to shunt a septal defect of a patient's heart, for example, by creating a shunt in the atrial septum of a neonate with hypoplastic left heart syndrome (HLHS). Amplatz discloses that increasing mixing of pulmonary and systemic venous blood improves oxygen saturation. Amplatz discloses that depending on the hemodynamics, the shunting passage can later be closed by an occluding device. Amplatz is silent on the treatment of CHF or the reduction of left atrial pressure, as well as on means for regulating the rate of blood flow through the device.

U.S. Patent Publication No. 2005/0165344 to Dobak, III discloses an apparatus for treating heart failure that includes a conduit positioned in a hole in the atrial septum of the heart, to allow flow from the left atrium into the right atrium. Dobak discloses that the shunting of blood will reduce left atrial pressures, thereby preventing pulmonary edema and progressive left ventricular dysfunction, and reducing LVEDP. Dobak discloses that the conduit may include a self-expandable tube with retention struts, such as metallic arms that exert a slight force on the atrial septum on both sides and pinch or clamp the valve to the septum, and a one-way valve member, such as a tilting disk, bileaflet design, or a flap valve formed of fixed animal pericardial tissue. However, Dobak states that a valved design may not be optimal due to a risk of blood stasis and thrombus formation on the valve, and that valves can also damage blood components due to turbulent flow effects. Dobak does not provide any specific guidance on how to avoid such problems.

SUMMARY OF THE INVENTION

Embodiments of the present invention provide hourglass-shaped devices for reducing left atrial pressure, and methods of making and using the same. As elaborated further herein, such reductions in left atrial pressure may increase cardiac output, relieve pulmonary congestion, and lower pulmonary artery pressure, among other benefits. The inventive devices are configured for implantation through the atrial septum, and particularly through the middle of the fossa ovalis, away from the surrounding limbus, inferior vena cava (IVC), and atrial wall. The devices are configured to provide one-way blood flow from the left atrium to the right atrium when the pressure in the left atrium exceeds the pressure in the right atrium, and thus decompress the left atrium. Such a lowering of left atrial pressure may offset abnormal hemodynamics associated with CHF, for example, to reduce congestion as well as the occurrence of acute cardiogenic pulmonary edema (ACPE), which is a severe manifestation of CHF in which fluid leaks from pulmonary capillaries into the interstitium and alveoli of the lung. In particular, lowering the left atrial pressure may improve the cardiac function by:

(1) Decreasing the overall pulmonary circulation pressure, thus decreasing the afterload on the heart, (2) Increasing cardiac output by reducing left ventricular end systolic dimensions, and (3) Reducing the left ventricular end-diastolic pressure (LVEDP) and pulmonary artery pressure (PAP), which in turn may enable the heart to work more efficiently and over time increase cardiac output. For example, the oxygen uptake of the myocardium may be reduced, creating a more efficient working point for the myocardium.

As described in further detail below, the devices provided herein comprise an hourglass or "diabolo" shaped stent encapsulated with a biocompatible material, and secured (e.g., sutured) to a tissue valve. The stent, which may be formed of shape memory material, for example a shape memory metal such as NiTi, comprises a neck region disposed between two flared end regions. The tissue valve is coupled to a flared end region configured for implantation in the right atrium. Specifically, the device may be implanted by forming a puncture through the atrial septum, particularly through the fossa ovalis, and then percutaneously inserting the device therethrough such that the neck lodges in the puncture, the flared end to which the tissue valve is coupled engages the right side of the atrial septum, and the other flared end flanks the left side of the atrial septum (e.g., is spaced apart from and does not contact the left side of the atrial septum). Placement in the middle of the fossa ovalis is useful because the engagement of the right-side flared end with the atrial septum enhances the stability of the valve. The neck region and the flared end region for placement in the left atrium may each be covered with a biocompatible polymer, such as expanded polytetrafluoroethylene (ePTFE), polyurethane, DACRON (polyethylene terephthalate), silicone, polycarbonate urethane, or pericardial tissue from an equine, bovine, or porcine source, which is optionally treated so as to promote a limited amount of tissue ingrowth, e.g., of epithelial tissue or a neointima layer. The tissue valve is connected to the biocompatible polymer in the right-side flared end region, close to the neck region, and is preferably a tricuspid, bicuspid, or duckbill valve configured to allow blood to flow from the left atrium to the right atrium when the pressure in the left atrium exceeds that in the right atrium, but prevent flow from the right atrium to the left atrium. In preferred embodiments, the device is effective to maintain the pressure differential between the left atrium and right atrium to 15 mmHg or less.

Under one aspect of the present invention, a device for regulating blood pressure between a patient's left atrium and right atrium comprises an hourglass-shaped stent comprising a neck and first and second flared end regions, the neck disposed between the first and second end regions and configured to engage the fossa ovalis of the patient's atrial septum; and a one-way tissue valve coupled to the first flared end region and configured to shunt blood from the left atrium to the right atrium when blood pressure in the left atrium exceeds blood pressure in the right atrium. In accordance with one aspect of the invention, moving portions of the valve are disposed in the right atrium, joined to but spaced apart from the neck region.

The hourglass-shaped stent may include a shape memory material (e.g., metal) coated with a biocompatible polymer from a portion of the first flared end region, through the neck region, and through the second flared end region, and the tissue valve may extend between the first flared end region and the biocompatible polymer. Providing the tissue valve in the side of the device to be implanted in the right atrium (that is, in the first flared end region) may inhibit thrombus formation and tissue ingrowth by providing that the tissue valve, as well as the region where the tissue valve is secured (e.g., sutured) to the biocompatible polymer, is continuously flushed with blood flowing through the right atrium. By comparison, if the tissue valve was instead secured (e.g., sutured) to the biocompatible polymer in the neck region, then the interface between the two would contact the tissue of the fossa ovalis, which potentially would encourage excessive tissue ingrowth, create leakages, and cause inflammation. Moreover, tissue ingrowth into the neck region would cause a step in the flow of blood in the narrowest part of the device, where flow is fastest, which would increase shear stresses and cause coagulation. Instead providing the tissue valve entirely within the right atrial side of the device inhibits contact between the tissue valve and the tissue of the atrial septum and fossa ovalis. Further, any tissue that ingrows into the valve will not substantially affect blood flow through the device, because the valve is located in a portion of the device having a significantly larger diameter than the neck region. Moreover, if the biocompatible tissue were instead to continue on the portions of the frame positioned over the tissue valve, it may create locations of blood stasis between the leaflets of the tissue valve and the biocompatible material. Having the valve entirely on the right atrial side and without biocompatible material on the overlying frame enables continuous flushing of the external sides of the tissue valve with blood circulating in the right atrium.

The biocompatible material preferably promotes limited (or inhibits excessive) tissue ingrowth into the valve, the tissue ingrowth including an endothelial layer or neointima layer inhibiting thrombogenicity of the device. The endothelial or neointima layer may grow to a thickness of 0.2 mm or less, so as to render the material inert and inhibit hyperplasia.

The hourglass-shaped stent may include a plurality of sinusoidal rings interconnected by longitudinally extending struts. In some embodiments, when the shunt is deployed across the patient's atrial septum, the first flared end region protrudes 5.5 to 7.5 mm into the right atrium. The second flared end region may protrude 2.5 to 7 mm into the left atrium. The neck may have a diameter of 4.5 to 5.5 mm. The first flared end region may have a diameter between 9 and 13 mm, and the second flared end region may have a diameter between 8 and 15 mm. The first and second flared end regions each may flare by about 50 to 120 degrees. For example, in one embodiment, the first flared end region flares by about 80 degrees, that is, the steepest part of the outer surface of the first flared end region is at an angle of approximately 40 degrees relative to a central longitudinal axis of the device. The second flared end region may flare by about 75 degrees, that is, the steepest part of the outer surface of the second flared end region may be at an angle of approximately 37.5 degrees relative to the central longitudinal axis of the device.

The inlet of the tissue valve may be about 1-3 mm from a narrowest portion of the neck region, and the outlet of the tissue valve may be about 5-8 mm from the narrowest portion of the neck region. The tissue valve may comprise a sheet of tissue having a flattened length of about 10-16 mm, and the sheet of tissue may be folded and sutured so as to define two or more leaflets each having a length of about 5-8 mm. For example, the tissue sheet may have a flattened length of no greater than 18 mm, for example, a length of 10-16 mm, or 12-14 mm, or 14-18 mm, and may be folded and sutured to define two or more leaflets each having a length of, for example, 9 mm or less, or 8 mm or less, or 7 mm or less, or 6 mm or less, or even 5 mm or less, e.g., 5-8 mm. The tissue sheet may have a flattened height no greater than 10 mm, for example, a height of 2-10 mm, or 4-10 mm, or 4-8 mm, or 6-8 mm, or 4-6 mm. The tissue sheet may have a flattened area of no greater than 150 square mm, for example, 60-150 square mm, or 80-120 square mm, or 100-140 square mm, or 60-100 square mm.

The hourglass-shaped stent may be configured to transition between a collapsed state suitable for percutaneous delivery and an expanded state when deployed across the patient's fossa ovalis. The stent may have an hourglass configuration in the expanded state. The hourglass configuration may be asymmetric. The stent may be configured for implantation through the middle of the fossa ovalis, away from the surrounding limbus, inferior vena cava, and atrial wall.

The one-way tissue valve may have two or more leaflets, e.g., may have a tricuspid or bicuspid design. The one-way tissue valve may comprise pericardial tissue, which in one embodiment may consist primarily of the mesothelial and loose connective tissue layers, and substantially no dense fibrous layer. Note that the dimensions of the hourglass-shaped device may be significantly smaller than those of replacement aortic valves, which may for example have a diameter of 23 mm and require the use of larger, thicker valve leaflets to maintain the higher stresses generated by the combination of higher pressures and larger diameters. By comparison, the inventive device has much smaller dimensions, allowing the use of thinner tissue (e.g., about one third the thickness of tissue used in a replacement aortic valve), for example, pericardial tissue in which the external dense fibrous layer is delaminated and the mesothelial and loose connective tissue is retained.

Under another aspect of the present invention, a device for regulating blood pressure between a patient's left atrium and right atrium includes a stent comprising a neck region and first and second flared end regions, the neck region disposed between the first and second end regions and configured to engage the fossa ovalis of the patient's atrial septum; a biocompatible material disposed on the stent in the neck and the second flared end region and a portion of the first flared end region; and a one-way tissue valve configured to shunt blood from the left atrium to the right atrium when blood pressure in the left atrium exceeds blood pressure in the right atrium, the valve having an outlet coupled to the first flared end region and an inlet coupled to an edge of the biocompatible material, the valve and the biocompatible material defining a continuous sheath that inhibits excessive tissue ingrowth into the valve and channels blood flow through the valve. In one embodiment, the edge of the biocompatible material is about 1-3 mm, e.g., 2 mm, from a narrowest portion of the neck region.

Under another aspect, a method of treating a subject with heart pathology comprises: providing a device having first and second flared end regions and a neck region disposed therebetween, and a tissue valve coupled to the first flared end region; deploying the device across a puncture through the subject's fossa ovalis such that the neck region is positioned in the puncture, the first flared end region is disposed in, and engages, the atrial septum, and the second flared end region is disposed in, and flanks, the atrial septum; and reducing left atrial pressure and left ventricular end diastolic pressure by shunting blood from the left atrium to the right atrium through the device when the left atrial pressure exceeds the right atrial pressure.

Subjects with a variety of heart pathologies may be treated with, and may benefit from, the inventive device. For example, subjects with myocardial infarction may be treated, for example by deploying the device during a period immediately following the myocardial infarction, e.g., within six months after the myocardial infarction, or within two weeks following the myocardial infarction. Other heart pathologies that may be treated include heart failure and pulmonary congestion. Reducing the left atrial pressure and left ventricular end diastolic pressure may provide a variety of benefits, including but not limited to increasing cardiac output; decreasing pulmonary congestion; decreasing pulmonary artery pressure; increasing ejection fraction; increasing fractional shortening; and decreasing left ventricle internal diameter in systole. Means may be provided for measuring such parameters.

Such methods may include identifying the middle of the fossa ovalis of the atrial septum by pressing a needle against the fossa ovalis to partially tent the fossa ovalis; and puncturing the middle of the fossa ovalis with the needle.

Under yet another aspect of the present invention, a method of making a device comprises: providing a tube of shape-memory metal; expanding the tube on a mandrel to define first and second flared end regions and a neck therebetween, and heating the expanded tube to set the shape; coating the neck and second flared end region with a biocompatible material; providing a valve of animal pericardial tissue having leaflets fixed in a normally closed position; and securing an inlet of the valve to the first flared end region and to the biocompatible polymer at the neck region. The tube may be laser cut and may include a plurality of sinusoidal rings connected by longitudinally extending struts, and the valve may be sutured to the struts and to the biocompatible material to form a passage for blood.

BRIEF DESCRIPTION OF DRAWINGS

FIGS. 3B-3E illustrate plan views of sheets of material for use in preparing tissue valves, according to some embodiments of the present invention.

DETAILED DESCRIPTION

Figure 1A:
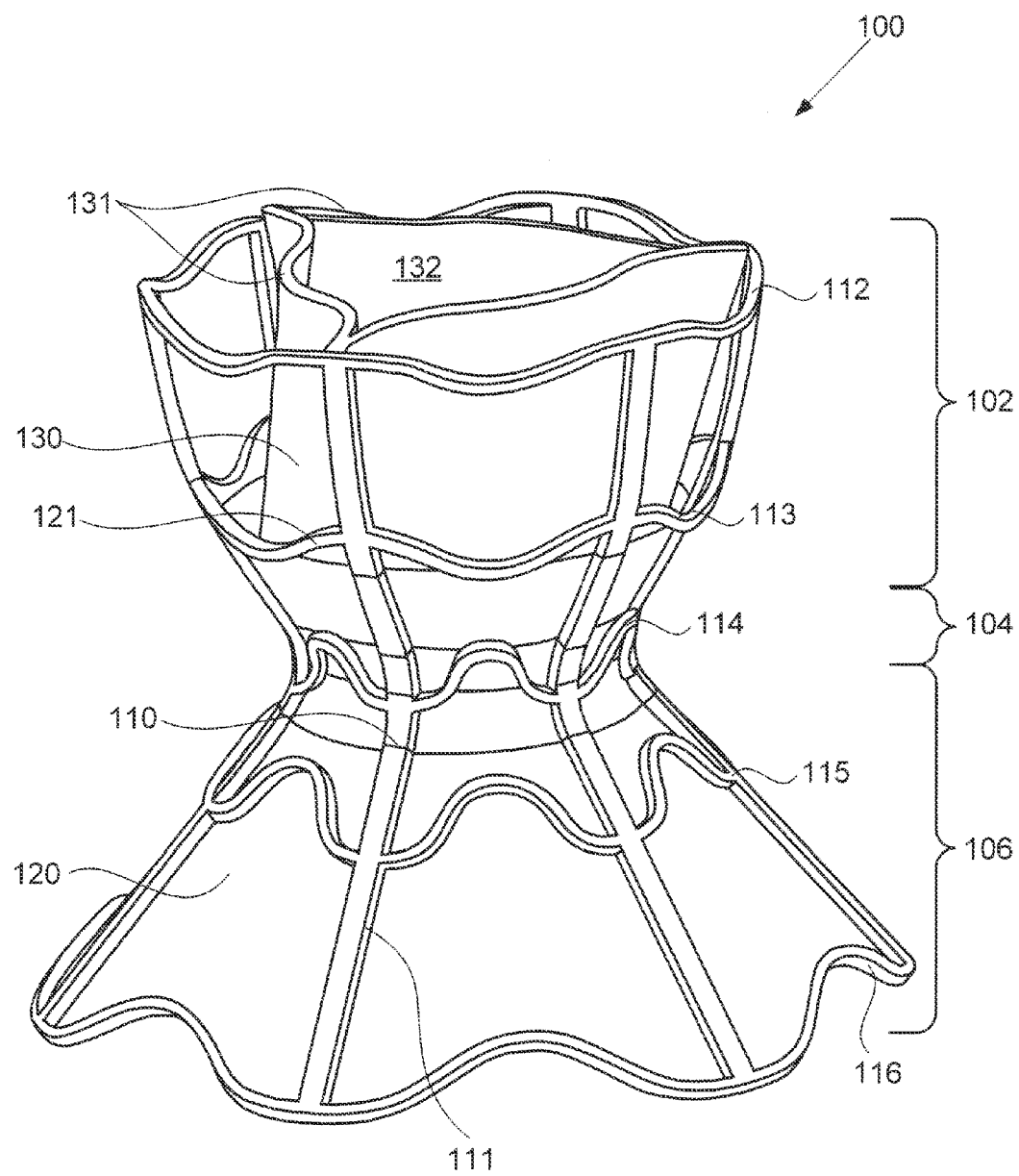
FIGS. 1A-1D illustrate perspective views of an hourglass-shaped device having a tricuspid valve, according to some embodiments of the present invention.

Embodiments of the present invention are directed to devices that reduce left atrial pressure, and thus may be useful in treating subjects suffering from congestive heart failure (CHF) or other disorders associated with elevated left atrial pressure. Specifically, the inventive device includes an hourglass or "diabolo" shaped stent, preferably formed of a shape memory metal, and a biocompatible valve coupled thereto. The stent is configured to lodge securely in the atrial septum, preferably the fossa ovalis, and the valve is configured to allow one-blood flow from the left atrium to the right atrium, preferably through the fossa ovalis, when blood pressure in the left atrium exceeds that on the right. Usefully, the inventive devices are configured so as to reduce blood pressure in the left atrium even when the pressure differential therebetween is relatively low; to provide a smooth flow path with a large valve opening, thus inhibiting turbulence and high shear stresses that would otherwise promote thrombus formation; to seal securely with rapid valve closure when the left and right atrial pressures equalize or the right atrial pressure exceeds left atrial pressure; and to have a relatively small implantation footprint so as to inhibit tissue overgrowth and inflammatory response.

First, a preferred embodiment of the inventive hourglass-shaped device will be described, and then methods of making, implanting, and using the same will be described. Then, the hemodynamic flow characteristics of some illustrative devices will be described, as well as a method for using an hourglass-shaped device to noninvasively determine left atrial pressure based on images of blood flowing through the implanted device. Some alternative embodiments will then be described. Lastly, an Example will be provided that describes a study performed on several animals into which an exemplary device was implanted, as compared to a group of control animals.

FIGS. 1A-1D illustrate perspective views of an illustrative embodiment of the inventive device. First, with reference to FIG. 1A, device 100 includes an hourglass-shaped stent 110 and tissue valve 130, illustratively, a tricuspid valve including three coapting leaflets. Device 100 has three general regions: first flared or funnel-shaped end region 102, second flared or funnel-shaped end region 106, and neck region 104 disposed between the first and second flared regions. Neck region 104 is configured to lodge in a puncture formed in the atrial septum, preferably in the fossa ovalis, using methods described in greater detail below. First flared end region 102 is configured to engage the right side of the atrial septum, and second flared end region 106 is configured to flank the left side of the atrial septum, when implanted. The particular dimensions and configurations of neck region 104 and first and second flared end regions 102, 106 may be selected so as to inhibit the formation of eddy currents when implanted, and thus inhibit thrombus formation; to inhibit tissue ingrowth in selected regions; to promote tissue ingrowth in other selected regions; and to provide a desirable rate of blood flow between the left and right atria.

Hourglass-shaped stent 110 is preferably formed of a shape memory metal, e.g., NITINOL, or any other suitable material known in the art. Stent 110 includes a plurality of sinusoidal rings 112-116 interconnected by longitudinally extending struts 111. Rings 112-116 and struts 111 may be of unitary construction, that is, entire stent 110 may be laser cut from a tube of shape memory metal. As can be seen in FIG. 1A, neck region 104 and second flared end region 106 are covered with biocompatible material 120, for example a sheet of a polymer such as expanded polytetrafluoroethylene (ePTFE), silicone, polycarbonate urethane, DACRON (polyethylene terephthalate), or polyurethane, or of a natural material such as pericardial tissue, e.g., from an equine, bovine, or porcine source. Specifically, the region extending approximately from sinusoidal ring 113 to sinusoidal ring 116 is covered with biocompatible material 120. Material 120 preferably is generally smooth so as to inhibit thrombus formation, and optionally may be impregnated with carbon so as to promote tissue ingrowth. Preferably, portions of stent 110 associated with first flared end region 102 are not covered with the biocompatible material, but are left as bare metal, so as to inhibit the formation of stagnant flow regions in the right atrium that otherwise and to provide substantially free blood flow around leaflets 131, so as to inhibit significant tissue growth on leaflets 131. The bare metal regions of stent 110, as well as any other regions of the stent, optionally may be electropolished or otherwise treated so as to inhibit thrombus formation, using any suitable method known in the art.

An inlet end of tissue valve 130 is coupled to stent 110 in first flared end region 102. In the illustrated embodiment, tissue valve 130 is a tricuspid valve that includes first, second, and third leaflets 131 defining valve opening 132. Other embodiments, illustrated further below, may include a bicuspid or duckbill valve, or other suitable valve construction. However, it is believed that tricuspid valves may provide enhanced leaflet coaptation as compared to other valve types, such that even if the tissue valve stiffens as a result of tissue ingrowth following implantation, there may still be sufficient leaflet material to provide coaptation with the other leaflets and close the valve. Preferably, tissue valve 130 opens at a pressure of less than 1 mm Hg, closes at a pressure gradient of between 0-0.5 mm Hg, and remains closed at relatively high back pressures, for example at back pressures of at least 40 mm Hg. Tissue valve 130 may be formed using any natural or synthetic biocompatible material, including but not limited to pericardial tissue, e.g., bovine, equine, or porcine tissue, or a suitable polymer. Pericardial tissue, and in particular bovine pericardial tissue, is preferred because of its strength and durability. The pericardial tissue may be thinned to enhance compliance, for example as described in greater detail below, and may be fixed using any suitable method, for example, using glutaraldehyde or other biocompatible fixative.

Figure 1B:
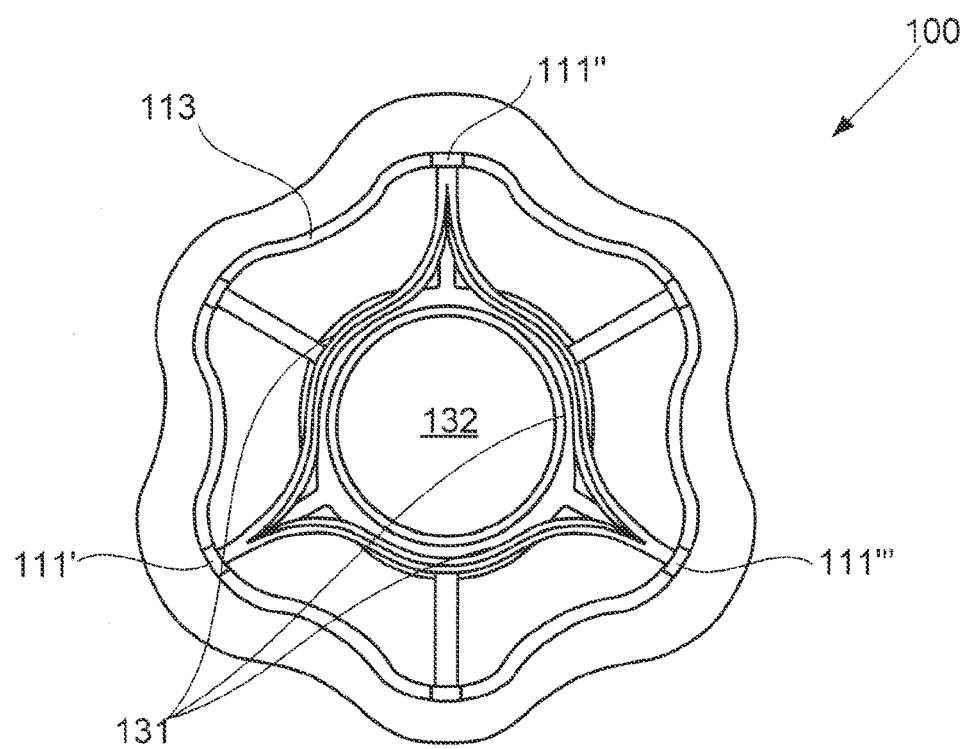

As shown in FIG. 1B, tissue valve 130 is coupled, e.g., sutured, to first, second, and third longitudinally extending struts 111', 111", and 111''' in the region extending between first (uppermost) sinusoidal ring 112 and second sinusoidal ring 113. Referring to FIGS. 1A and 1D, tissue valve 130 is also coupled to the upper edge of biocompatible material 120, at or near sinusoidal ring 113, for example along line 121 as shown. As such, tissue valve 130 and biocompatible material 120 together provide a smooth profile to guide blood flow from the left atrium to the right atrium, that is, from the second flared end region 106, through neck region 104, and through first flared end region 102. In accordance with one aspect of the invention, the inlet to tissue valve 130 is anchored to neck region 104, such that leaflets 131 extend into the right atrium. In this manner, any eccentricities that may arise from the out-of-roundness of the puncture through the fossa ovalis during implantation will not be transferred to the free ends of leaflets 131, thus reducing the risk that any eccentricity of the stent in neck region 104 could disturb proper coaptation of the valve leaflets.

Figure 1C:
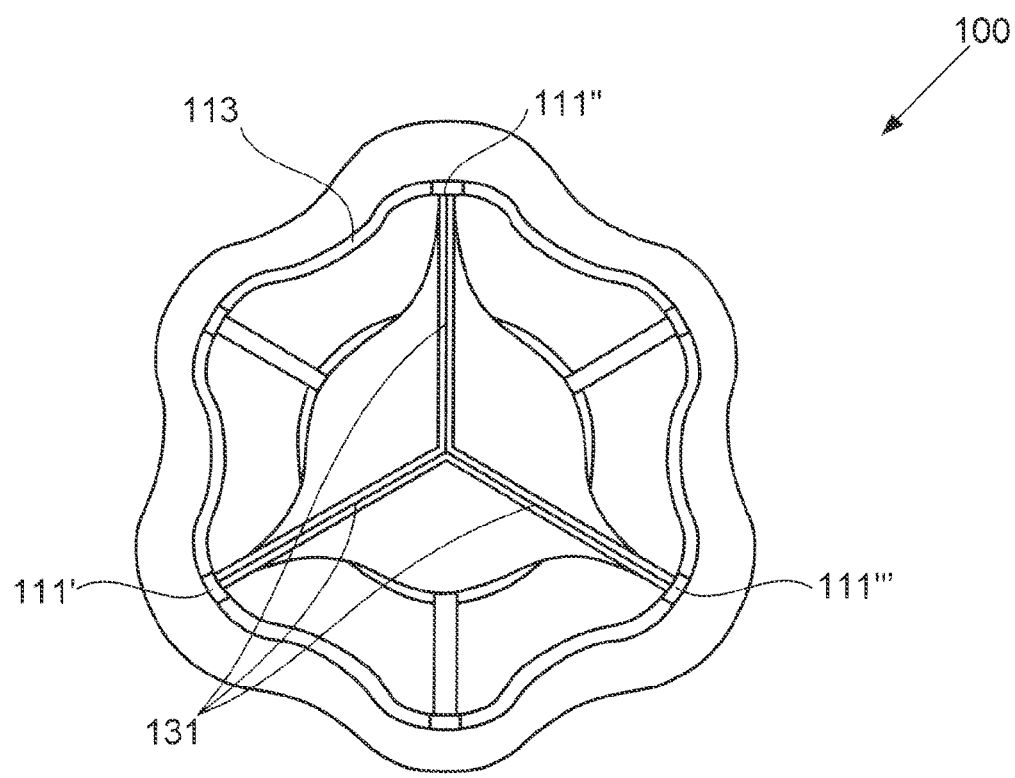
Figure 1D:
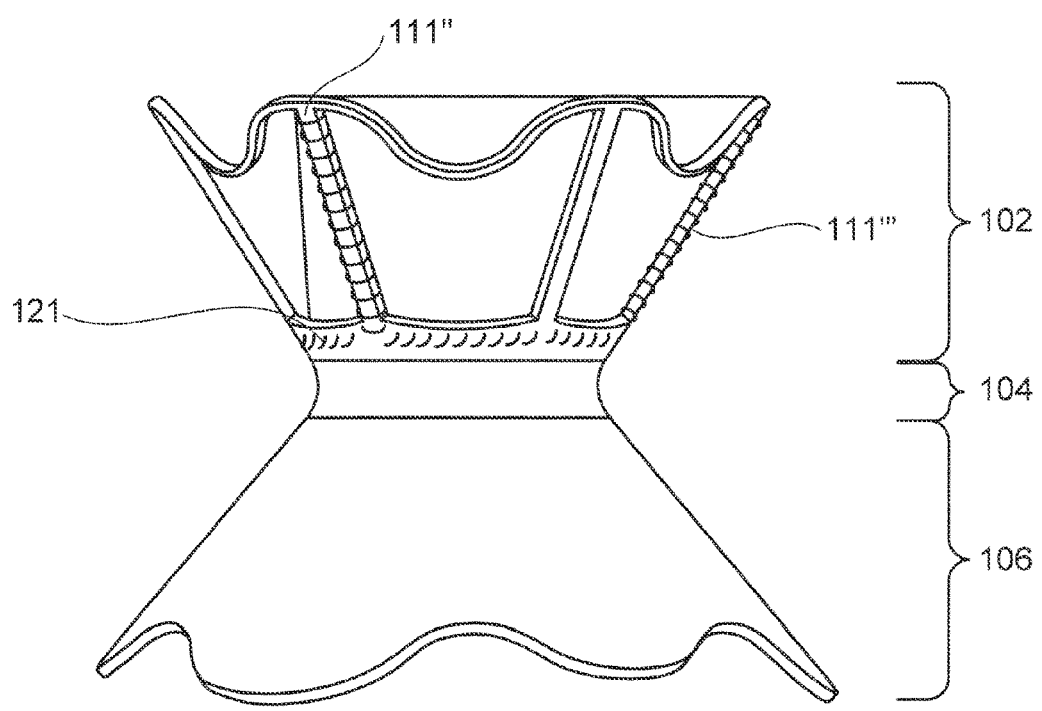

FIGS. 1A and 1B illustrate device 100 when tissue valve 130 is in an open configuration, in which leaflets 131 are in an open position to permit flow, and FIG. 1C illustrates device 100 when tissue valve 130 is in a closed configuration, in which leaflets 131 are in a closed position to inhibit flow. Tissue valve 130 is configured to open when the pressure at second flared end region 106 exceeds that at first flared end region 102. Preferably, however, tissue valve 130 is configured to close and therefore inhibit flow in the opposite direction, i.e., to inhibit flow from first flared end region 102, through neck region 104, and through second flared end region 104, when the pressure at the first flared end region exceeds that of the second. Among other things, such a feature is expected to inhibit passage of thrombus from the right atrium to the left atrium, which could cause stroke or death. Moreover, allowing flow of blood with low oxygenation from right to left would further aggravate CHF. Further, tissue valve 130 preferably is configured to close and therefore inhibit flow in either direction when the pressures at the first and second flared end regions are approximately equal. Preferably, tissue valve 130 is sized and has dynamic characteristics selected to maintain a pressure differential between the left and right atria of 15 mm Hg or less.

To achieve such flow effects, as well as reduce complexity of device fabrication, tissue valve 130 preferably is a tricuspid valve, as is illustrated in FIGS. 1A-1D, but alternatively may be a bicuspid valve, for example a duckbill valve, or a mitral valve, as described here after with respect to FIGS. 8A-8C and 9. For example, as described in greater detail below with respect to FIGS. 3A-3E, tissue valve 130 may be formed of a single piece of thinned animal pericardial tissue that is sutured along at least one edge to form an open-ended conical or ovoid tube, and then three-dimensionally fixed to assume a normally closed position. The inlet or bottom (narrower) end of the tube may be coupled, e.g., sutured, to biocompatible material 120 at or near sinusoidal ring 113, and the sides of the tube optionally may be sutured to struts 111', 111", and 111''', as illustrated in FIG. 1D (strut 111' not shown in FIG. 1D). In one embodiment, the bottom end of the tube is sutured to biocompatible material 120 along substantially straight line 121 that is approximately 2-3 mm to the right of the narrowest portion of neck region 104. Without wishing to be bound by theory, it is believed that such a location for line 121 may be sufficiently large as to inhibit tissue from atrial septum 210 from growing into tissue valve 130. In another embodiment (not illustrated), the bottom end of tissue valve 130 is secured, e.g., sutured to biocompatible material 120 along a curve that follows the shape of sinusoidal ring 113. During use, the outlet or upper (wider) end of the tube may open and close based on the pressure differential between the inlet and outlet ends, that is, between the left and right atria when implanted. Other suitable valve configurations may include bicuspid valves, duckbill valves, sleeve (windsock) valves, flap valves, and the like.

As noted above, hourglass-shaped device 100 preferably is configured for implantation through the fossa ovalis of the atrial septum, particularly through the middle of the fossa ovalis. As known to those skilled in the art, the fossa ovalis is a thinned portion of the atrial septum caused during fetal development of the heart, which appears as an indent in the right side of the atrial septum and is surrounded by a thicker portion of the atrial septum. While the atrial septum itself may be several millimeters thick and muscular, the fossa ovalis may be only approximately one millimeter thick, and is formed primarily of fibrous tissue. Advantageously, because the fossa ovalis comprises predominantly fibrous tissue, that region of the atrial septum is not expected to undergo significant tension or contraction during the cardiac cycle, and thus should not impose significant radial stresses on stent 110 that could lead to stress-induce cracking. In addition, the composition of the fossa ovalis as primarily fibrous tissue is expected to avoid excessive endothelialization after implantation.

Figure 2A:
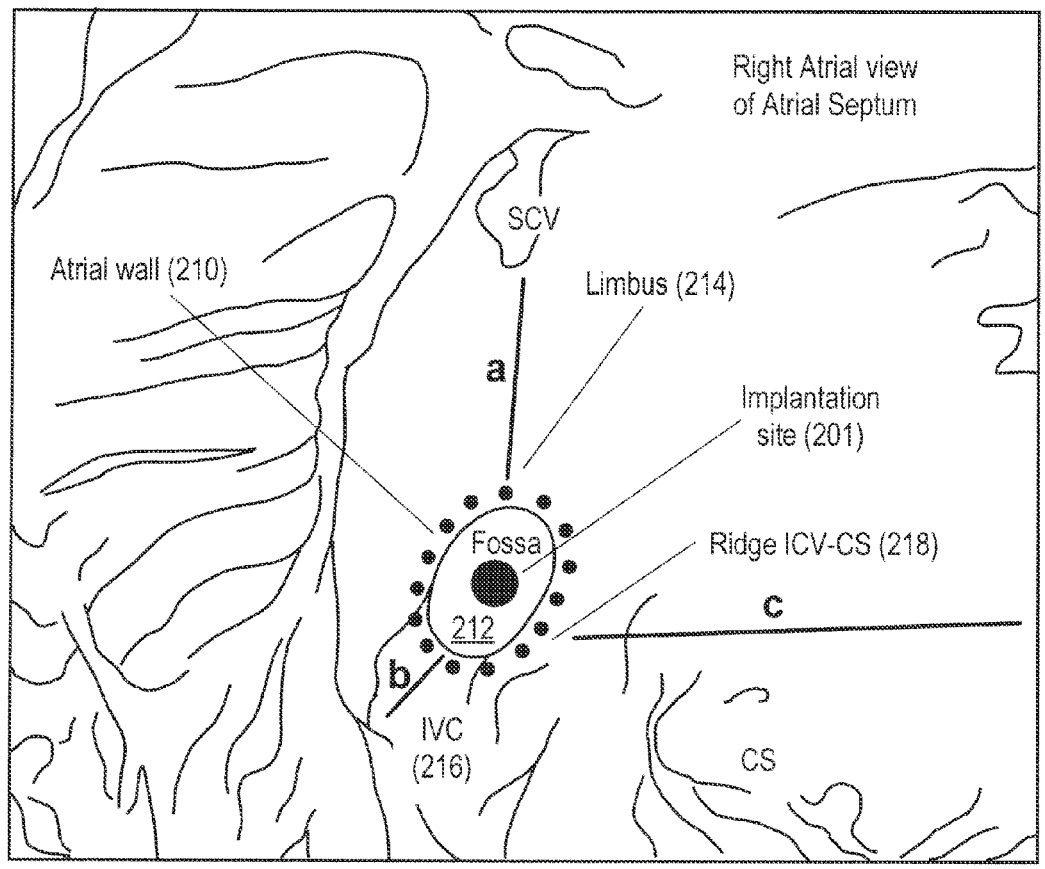
FIG. 2A schematically illustrates a plan view of the right atrial side of the atrial septum, including a site for implanting an hourglass-shaped device through the middle of the fossa ovalis.
Figure 2B:
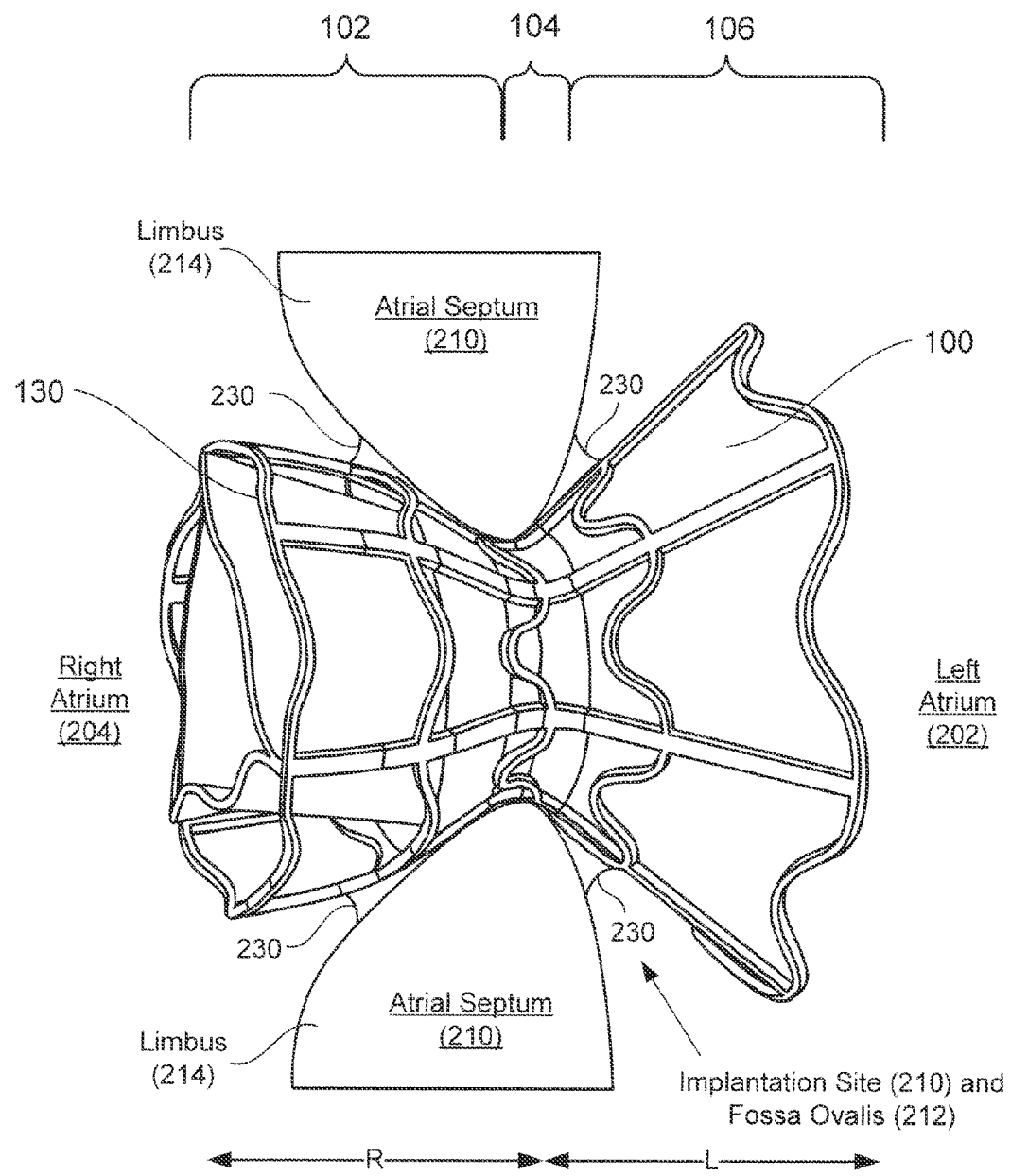
FIG. 2B schematically illustrates a cross-sectional view of the hourglass-shaped device of FIGS. 1A-1D positioned in the fossa ovalis of the atrial septum, according to some embodiments of the present invention.

In some embodiments of the present invention, hourglass-shaped device 100 is asymmetrically shaped to take advantage of the natural features of atrial septum 210 near the fossa ovalis, and to provide suitable flow characteristics. FIG. 2A illustrates a plan view of the right atrial side of the atrial septum 210, including an implantation site 201 through the fossa ovalis 212. Preferably, the implantation site 201 is through the middle of the fossa ovalis 212, so that the device may be implanted at a spaced distance from the surrounding limbus 214, inferior vena cava (IVC) 216, and atrial wall 210. For example, as illustrated in FIG. 2B, first flared end region 102 is configured to be implanted in right atrium 204 and may be tapered so as to have a more cylindrical shape than does second flared end region 106, which is configured to be implanted in left atrium 202. The more cylindrical shape of first flared end region 102 may enhance opening and closing of tissue valve 130, while reducing risk of the tissue valve falling back towards stent 110; may increase the proportion of tissue valve 130 that moves during each open-close cycle, and thus inhibit tissue growth on the valve; and may reduce or inhibit contact between first flared end region 102 and the limbus 214 of the fossa ovalis 212, that is, between first flared end region 102 and the prominent margin of the fossa ovalis, while still anchoring device 100 across atrial septum 210. The more cylindrical shape of first flared end region 102 further may reduce or inhibit contact between first flared end region 102 and the right atrial wall, as well as the ridge 218 separating the coronary sinus from the inferior vena cava (IVC) (shown in FIG. 2A but not FIG. 2B). Additionally, in some embodiments the first flared end region 102 substantially does not extend beyond the indent of the fossa ovalis in the right atrium, and therefore substantially does not restrict blood flow from the IVC 216.

In accordance with one aspect of the invention, device 100 preferably is configured so as to avoid imposing significant mechanical forces on atrial septum 210 or atria 202, 204, allowing the septum to naturally deform as the heart beats. For example, muscular areas of septum 210 may change by over 20% between systole and diastole. It is believed that any significant mechanical constraints on the motion of atrial septum 210 in such areas would lead to the development of relatively large forces acting on the septum and/or on atrial tissue that contacts device 100, which potentially would otherwise cause the tissue to have an inflammatory response and hyperplasia, and possibly cause device 100 to eventually lose patency. However, by configuring device 100 so that neck region may be implanted entirely or predominantly in the fibrous tissue of the fossa ovalis 212, the hourglass shape of device 100 is expected to be sufficiently stable so as to be retained in the septum, while reducing mechanical loads on the surrounding atrial septum tissue 210. As noted elsewhere herein, tissue ingrowth from atrial septum 210 in regions 230 may further enhance binding of device 100 to the septum.

Also, for example, as illustrated in FIG. 2B, neck region 104 of device 100 is significantly narrower than flared end regions 102, 106, facilitating device 100 to "self-locate" in a puncture through atrial septum 210, particularly when implanted through the fossa ovalis. In some embodiments, neck region 104 may have a diameter suitable for implantation in the fossa ovalis, e.g., that is smaller than the fossa ovalis, and that also is selected to inhibit blood flow rates exceeding a predetermined threshold. For example, the smallest diameter of neck 104 may be between about 3 and 6 mm, e.g., between about 4.5 mm and 5.5 mm, preferably between about 4.5 mm and 5.5 mm. For example, it is believed that diameters of less than about 4.5 mm may in some circumstances not allow sufficient blood flow through the device to decompress the left atrium, and may reduce long-term patency of device 100, while diameters of greater than about 5.5 mm may allow too much blood flow. For example, flow rates of greater than 1.2 liters/minute, or even greater than 1.0 liters/minute are believed to potentially lead to remodeling of the right atrium. Preferably, the effective diameter at the narrowest point in device 100, i.e., the narrowest diameter provided by the combination of neck 104 and biocompatible material 120 is about 4.5 mm to 4.8 mm. Such a diameter range is expected to provide a flow rate of about 0.80 liters/minute or less following ingrowth of septal tissue, which may anchor device 100 in place, and which may result in an overall diameter reduction of about 1.0 mm over time.

In some embodiments, the length of first flared end region 102 also may be selected to protrude into the right atrium by a distance selected to inhibit tissue ingrowth that may otherwise interfere with the operation of tissue valve 130. For example, distance R between the narrowest portion of neck region 104 and the end of first flared region 102 may be approximately 5.0 to 9.0 mm, for example about 5.5 to about 7.5 mm, or about 6 mm, so as not to significantly protrude above the limbus of fossa ovalis 212. Second flared end region 106 preferably does not significantly engage the left side of atrial septum 210, and distance L may be between 2.0 and 6.0 mm, for example about 2.5 to 7 mm, or about 3.0 mm. It is believed that configuring first and second flared end regions 102, 106 so as to extend by as short a distance as possible into the right and left atria, respectively, while still maintaining satisfactory flow characteristics and stabilization in atrial septum 210, may reduce blockage of flow from the inferior vena cava (IVC) in the right atrium and from the pulmonary veins in the left atrium. In one illustrative embodiment, distance R is about 6.0 mm and distance L is about 3.0 mm. In some embodiments, the overall dimensions of device 100 may be 10-20 mm long (L+R, in FIG. 2B), e.g., about 12-18 mm, e.g., about 14-16 mm, e.g., about 15 mm.

The diameters of the first and second flared end regions further may be selected to stabilize device 100 in the puncture through atrial septum 210, e.g., in the puncture through fossa ovalis 212. For example, first flared end region 102 may have a diameter of 10-15 mm at its widest point, e.g., about 9.0-13 mm; and second flared end region 106 may have a diameter of 10-20 mm at its widest point, e.g., about 13-15 mm. The largest diameter of first flared end region 102 may be selected so as to avoid mechanically loading the limbus of the fossa ovalis 212, which might otherwise cause inflammation. The largest diameter of second flared end region 106 may be selected so as to provide a sufficient angle between first and second flared end regions 102, 106 to stabilize device 100 in the atrial septum, while limiting the extent to which second flared end region 106 protrudes into the left atrium (e.g., inhibiting interference with flow from the pulmonary veins), and providing sufficient blood flow from the left atrium through neck region 104. In one embodiment, the angle between the first and second flared end regions is about 50-90 degrees, e.g., about 60 to 80 degrees, e.g., about 70 degrees. Such an angle may stabilize device 100 across the fossa ovalis, while inhibiting excessive contact between the device and the atrial septum. Such excessive contact might cause inflammation because of the expansion and contraction of the atrial septum during the cardiac cycle, particularly between diastole and systole. In one embodiment, the first flared end region subtends an angle of approximately 80 degrees, that is, the steepest part of the outer surface of the first flared end region is at an angle of approximately 40 degrees relative to a central longitudinal axis of the device. The second flared end region may subtend an angle of approximately 75 degrees, that is, the steepest part of the outer surface of the second flared end region is at an angle of approximately 37.5 degrees relative to the central longitudinal axis of the device.

Tissue valve 130 is preferably configured such that when closed, leaflets 131 define approximately straight lines resulting from tension exerted by stent 110 across valve opening 132, as illustrated in FIG. 1C. Additionally, the transition between tissue valve 130 and biocompatible material 120 preferably is smooth, so as to reduce turbulence and the possibility of flow stagnation, which would increase coagulation and the possibility of blockage and excessive tissue ingrowth. As pressure differentials develop across tissue valve 130 (e.g., between the left and right atria), blood flow preferably follows a vector that is substantially perpendicular to the tension forces exerted by stent 110, and as such, the equilibrium of forces is disrupted and leaflets 131 start to open. As the leaflets open, the direction of tension forces exerted by stent 110 change, enabling an equilibrium of forces and support of continuous flow. An equilibrium position for each pressure differential is controlled by the geometry of tissue valve 130 and the elastic behavior of stent 110. When a negative pressure differential (right atrial pressure greater than left atrial pressure) develops, valve leaflets 131 are coapt, closing the tissue valve and the prevention of right to left backflow.

When device 100 is implanted across the atrial septum, as illustrated in FIG. 2B, left atrial pressures may be regulated in patients having congestive heart failure (CHF). For example, device 100 may reduce pressure in the left atrium by about 2-5 mmHg immediately following implantation. Such a pressure reduction may lead to a long-term benefit in the patient, because a process then begins by which the lowered left atrial pressure reduces the transpulmonary gradient, which reduces the pulmonary artery pressure. However, the right atrial pressure is not significantly increased because the right atrium has a relatively high compliance. Furthermore, the pulmonary capillaries may self-regulate to accept high blood volume if needed, without increasing pressure. When the left atrial pressure is high, the pulmonary capillaries constrict to maintain the transpulmonary gradient, but as the left atrial pressure decreases, and there is more blood coming from the right atrium, there are actually higher flow rates at lower pressures passing through the pulmonary circulation. After a period of between a few hours and a week following implantation of device 100, the pulmonary circulation has been observed to function at lower pressures, while the systemic circulation maintains higher pressures and thus adequate perfusion. The resulting lower pulmonary pressures, and lower left ventricle end diastolic pressure (LVEDP) decrease the after load by working at lower pressures, resulting in less oxygen demand and less resistance to flow. Such small decreases in afterload may dramatically increase the cardiac output (CO) in heart failure, resulting in increased ejection fraction (EF). Moreover, because of the release in the afterload and in the pressures of the pulmonary circulation, the right atrial pressure decreases over time as well. Following myocardial infarction, the effect is even more pronounced, because the period after the infarction is very important for the remodeling of the heart. Specifically, when the heart remodels at lower pressures, the outcome is better.

In the region of contact between device 100 and atrial septum 210, preferably there is limited tissue growth. The connective tissue of atrial septum 210 is non-living material, so substantially no nourishing of cells occurs between the septum and device 100. However, local stagnation in flow may lead to limited cell accumulation and tissue growth where device 100 contacts atrial septum 210, for example in regions designated 230 in FIG. 2B. Such tissue growth in regions 230 may anchor device 210 across atrial septum 210. Additional, such tissue growth may cause the flow between the external surface of device 100 and atrial septum 210 to become smoother and more continuous, thus reducing or inhibiting further cell accumulation and tissue growth in regions 230. As noted above, first flared end region 102 of stent 110, e.g., between the line along which tissue valve 130 is coupled to biocompatible material 120 and first sinusoidal ring 112 preferably is bare metal. This configuration is expected to inhibit formation of stagnation points in blood flow in right atrium 204, that otherwise may lead to tissue growth on the external surfaces of leaflets 131 of tissue valve 130.

A method 300 of making device 100 illustrated in FIGS. 1A-1D and FIG. 2B will now be described with respect to FIGS. 3A-3E.

Figure 3A:
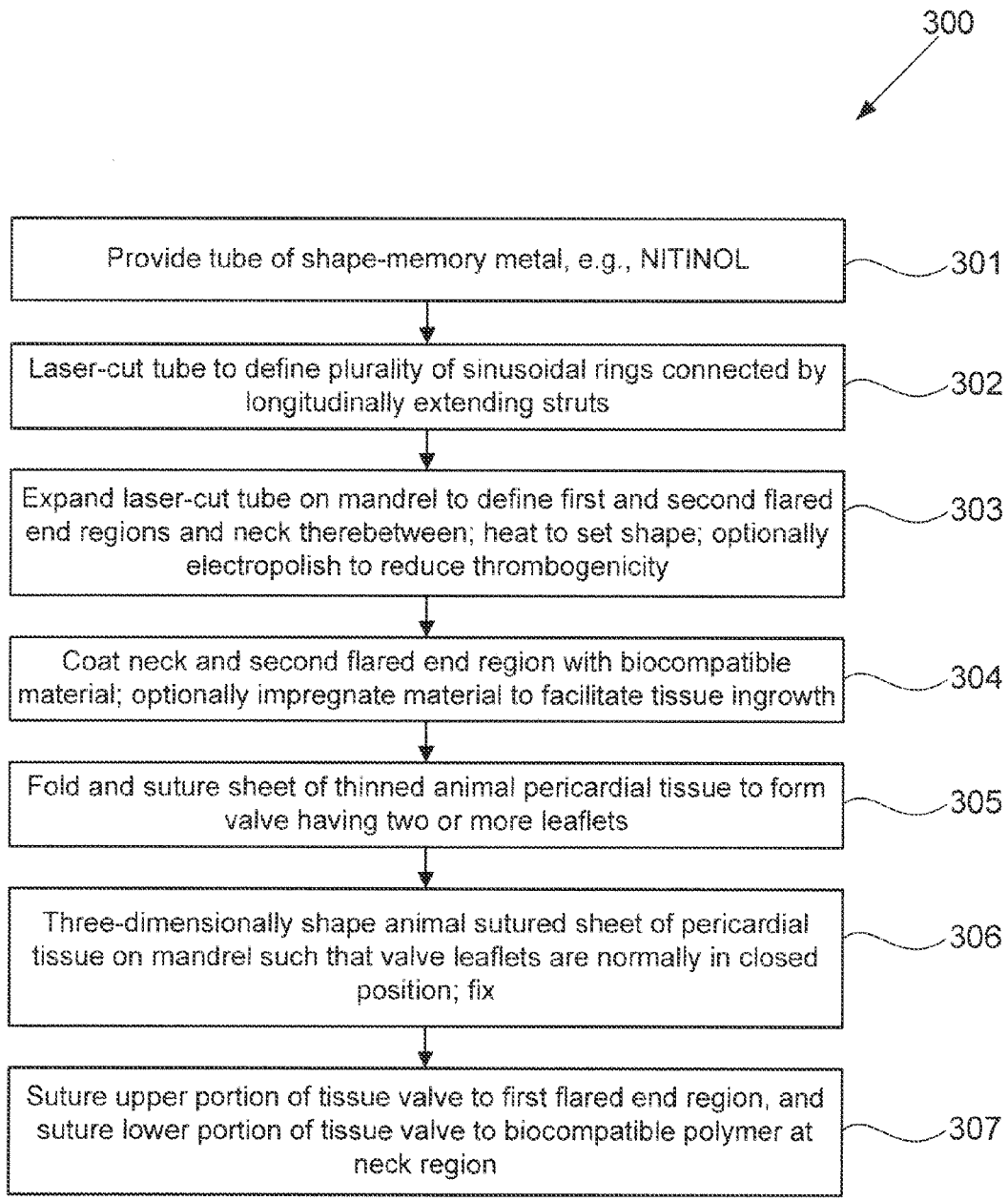
FIG. 3A is a flow chart of steps in a method of making an hourglass-shaped device, according to some embodiments of the present invention.

First, a tube of shape-memory material, e.g., a shape-memory metal such as nickel titanium (NiTi), also known as NITINOL, is provided (step 301 of FIG. 3A). Other suitable materials known in the art of deformable stents for percutaneous implantation may alternatively be used, e.g., other shape memory alloys, polymers, and the like. In one embodiment, the tube has a thickness of 0.25 mm.

Then, the tube is laser-cut to define a plurality of sinusoidal rings connected by longitudinally extending struts (step 302). For example, struts 111 and sinusoidal rings 112-116 illustrated in FIG. 1A may be defined using laser cutting a single tube of shape-memory metal, and thus may form an integral piece of unitary construction. Alternatively, struts Ill 1 and sinusoidal rings 112-116 may be separately defined from different pieces of shape-memory metal and subsequently coupled together.

Referring again to FIG. 3A, the laser-cut tube then is expanded on a mandrel to define first and second flared end regions and a neck therebetween, e.g., to define first end region 102, second end region 106, and neck region 104 as illustrated in FIG. 1A; the expanded tube then may be heated to set the shape of stent 110 (step 303). In one example, the tube is formed of NITINOL, shaped using a shape mandrel, and placed into an oven for 11 minutes at 530 C to set the shape. Optionally, the stent thus defined also may be electropolished to reduce thrombogenicity, or otherwise suitably treated. Such electropolishing may alternatively be performed at a different time, e.g., before shaping using the mandrel.

As shown in FIG. 3A, the neck and second flared end region of the stent then may be coated with a biocompatible material (step 304). Examples of suitable biocompatible materials include expanded polytetrafluoroethylene (ePTFE), polyurethane, DACRON (polyethylene terephthalate), silicone, polycarbonate urethane, and animal pericardial tissue, e.g., from an equine, bovine, or porcine source. In one embodiment, the stent is coated with the biocompatible material by covering the inner surface of the stent with a first sheet of ePTFE, and covering the outer surface of the stent with a second sheet of ePTFE. The first and second sheets first may be temporarily secured together to facilitate the general arrangement, e.g., using an adhesive, suture, or weld, and then may be securely bonded together using sintering to form a strong, smooth, substantially continuous coating that covers the inner and outer surfaces of the stent. Portions of the coating then may be removed as desired from selected portions of the stent, for example using laser-cutting or mechanical cutting. For example, as shown in FIG. 1A, biocompatible material 120 may cover stent 110 between sinusoidal ring 113 and sinusoidal ring 116, i.e., may cover neck region 104 and second flared end region 106, but may be removed between sinusoidal ring 113 and sinusoidal ring 112, i.e., may be removed from (or not applied to) first flared end region 102.

The biocompatible material facilitates funneling of blood from the left atrium to the right atrium by facilitating the formation of a pressure gradient across tissue valve 130, as well as providing a substantially smooth hemodynamic profile on both the inner and outer surfaces of device 100. Advantageously, this configuration is expected to inhibit the formation of eddy currents that otherwise may cause emboli to form, and facilitates smooth attachment of the device to the atrial septum, e.g., fossa ovalis. Biocompatible material 120 preferably is configured so as to direct blood flow from the left atrium, through neck region 104 and toward tissue valve leaflets 131. Biocompatible material 120 preferably also is configured so as to inhibit tissue growth from atrial septum 210 and surrounding tissue into device 100 and particularly toward tissue valve leaflets 131. In some embodiments, the biocompatible material 120 has a porosity that is preselected to allow limited cell growth on its surface; the cells that grow on such a surface preferably are endothelial cells that are exposed to blood and inhibit blood from coagulating on the biocompatible material. After such cells grow on the biocompatible material 120, the material preferably is substantially inert and thus not rejected by the body. Optionally, the biocompatible material may be impregnated with a second material that facilitates tissue ingrowth, e.g., carbon. Such impregnation may be performed before or after applying the biocompatible material to the stent.

Then, as shown in FIG. 3A, a valve having two or more leaflets, such as a tricuspid, bicuspid, or duckbill valve, or any other suitable valve, is formed by folding and suturing a sheet of thinned animal pericardial tissue, e.g., equine, bovine, or porcine material (step 305). FIGS. 3B-3E illustrate plan views of exemplary sheets of animal pericardial tissue that may be used to form tissue valves. Specifically, FIG. 3B illustrates an approximately semicircular sheet 310 of tissue for use in preparing a tricuspid tissue valve. Although the sheet 310 may be any suitable dimensions, in the illustrated embodiment the sheet has a width of 10-16 mm, a length of 6-8 mm. The opposing edges may be at an angle between 0-70 degrees relative to one another so that when the sheet is folded and those edges are secured, e.g., sutured together, sheet 310 forms a generally funnel-like shape having approximately the same angle as the first flared end region to which it is to be secured. FIG. 3C illustrates an embodiment similar to that of FIG. 3B, but in which sheet 320 also includes wings 321 providing additional tissue material in regions along the suture line that may be subjected to high stresses, as well as a curved top contour 322 that provides an extended region for coaptation between the leaflets when the valve is closed. Wings may be approximately 2-5 mm long, and extend 0.5-1.5 mm beyond the lateral edges of sheet 320. FIG. 3D illustrates an embodiment similar to that of FIG. 3C, e.g., that includes wings 331 that may be of similar dimension as wings 321, but in which sheet 330 lacks a curved top contour. Sutures 332 are shown in FIG. 3D. FIG. 3E illustrates a sheet 340 of tissue suitable for use in preparing a bicuspid tissue valve, that has a generally rectangular shape, for example having a width of 14-15 mm and a length of 6.0-7.0 mm. Other dimensions may suitably be used. For example, the tissue sheet may have a flattened length of no greater than 18 mm, for example, a length of 10-16 mm, or 12-14 mm, or 14-18 mm, and may be folded and sutured to define two or more leaflets each having a length of, for example, 9 mm or less, or 8 mm or less, or 7 mm or less, or 6 mm or less, or even 5 mm or less, e.g., 5-8 mm. The tissue sheet may have a flattened height no greater than 10 mm, for example, a height of 2-10 mm, or 4-10 mm, or 4-8 mm, or 6-8 mm, or 4-6 mm. The tissue sheet may have a flattened area of no greater than 150 square mm, for example, 60-150 square mm, or 80-120 square mm, or 100-140 square mm, or 60-100 square mm. In some exemplary embodiments, the sheet of tissue may have a generally trapezoidal or "fan" shape, so that when opposing edges are brought together and sutured together, the sheet has a general "funnel" shape, with a wide opening along the outlet or upper edge and a narrow opening along the inlet or lower edge. Note that other suitable methods of securing opposing edges of the sheet alternatively may be used, e.g., adhesive, welding, and the like.

The tissue may have a thickness, for example, of between 0.050 mm and 0.50 mm, for example, about 0.10 mm and 0.20 mm. Typically, harvested bovine pericardial tissue has a thickness between about 0.3 mm and 0.5 mm, which as is known in the art is a suitable thickness for high-stress applications such as construction of aortic valves. However, for use in the device of the present invention, it may be preferable to thin the pericardial tissue. For example, the stresses to which the valve leaflets are exposed in a device constructed in accordance with the present invention may be a small fraction (e.g., ½5th) of the stresses in an aortic valve application, because of the relatively large surface area of the leaflets and the relatively low pressure gradients across the device. For this reason, thinned pericardial tissue may be used, enabling construction of a more compliant valve that may be readily fixed in a normally closed position but that opens under relatively low pressure gradients. Additionally, the use of thinner leaflets is expected to permit the overall profile of the device to be reduced in when the device is compressed to the contracted delivery state, thereby enabling its use in a wider range of patients.

For example, harvested pericardial tissue typically includes three layers: the smooth and thin mesothelial layer, the inner loose connective tissue, and the outer dense fibrous tissue. The pericardial tissue may be thinned by delaminating and removing the dense fibrous tissue, and using a sheet of the remaining mesothelial and loose connective layers, which may have a thickness of 0.10 mm to 0.20 mm, to construct the tissue valve. The dense fibrous tissue may be mechanically removed, for example using a dermatome, grabbing tool, or by hand, and any remaining fibers trimmed.

The animal pericardial tissue then may be three-dimensionally shaped on a mandrel to define a tissue valve having valve leaflets that are normally in a closed position, and then fixed in that position using glutaraldehyde or other suitable substance (step 306). Excess glutaraldehyde may be removed using an anticalcification treatment, for example to inhibit the formation of calcium deposits on the tissue valve.

The outlet or upper (wider) portion of the tissue valve then may be secured, e.g., sutured, to the first flared end region, and the inlet or lower (narrower) portion of the tissue valve secured, e.g., sutured to the biocompatible polymer at the neck region (step 307). For example, as illustrated in FIGS. 1A-1D, the lower portion of tissue valve 130 may be secured using sutures to biocompatible material 120 at or near sinusoidal ring 113 (for example, along a line 121 approximately 2-3 mm to the right of the narrowest portion of neck region 104), and also may be sutured to elongated struts 111', 111", and 111''' so as to define a tricuspid valve having leaflets 131. Other suitable methods of securing the tissue valve to stent 110 and to biocompatible material 120 may alternatively be used. Preferably, tissue valve 130 is secured to device 100 such that, when implanted, the tissue valve is disposed substantially only in the right atrium. Such a configuration may facilitate flushing of the external surfaces of leaflets 131 with blood entering the right atrium. By comparison, it is believed that if leaflets 131 were instead disposed within neck region 104 or second flared end region 106, they might inhibit blood flow and/or gradually lose patency over time as a result of tissue ingrowth caused by the stagnation of blood around the leaflets.

Figure 4:
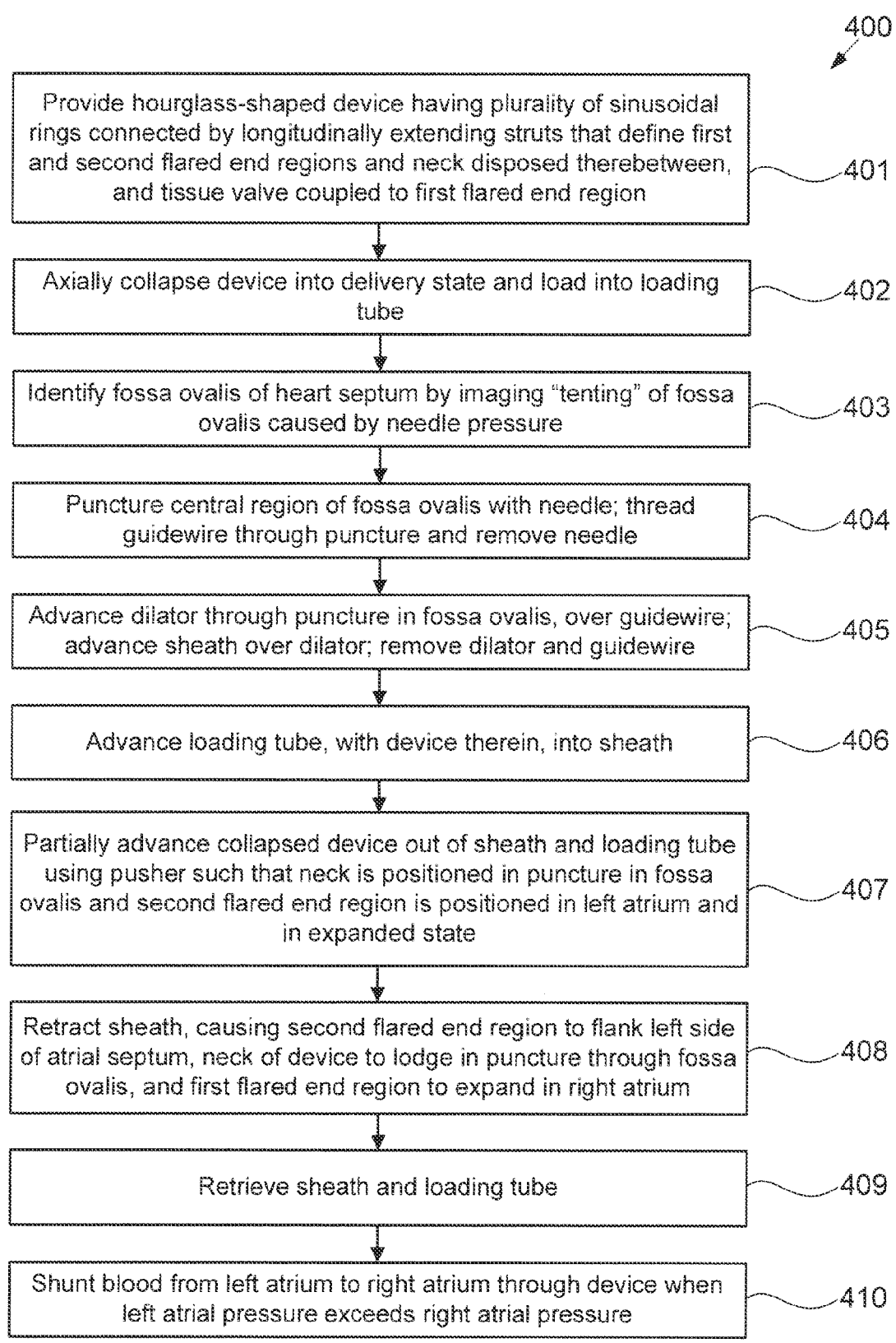
FIG. 4 is a flow chart of steps in a method of percutaneously implanting an hourglass-shaped device in a puncture through the fossa ovalis, according to some embodiments of the present invention.

A method 400 of using device 100 illustrated in FIGS. 1A-1D to reduce left atrial pressure in a subject, for example, a human having CHF, will now be described with reference to FIG. 4. Some of the steps of method 400 may be further elaborated by referring to FIGS. 5A-5D.

First, an hourglass-shaped device having a plurality of sinusoidal rings connected by longitudinally extending struts that define first and second flared end regions and a neck disposed therebetween, as well as a tissue valve coupled to the first flared end region, is provided (step 401). Such a device may be provided, for example, using method 300 described above with respect to FIGS. 3A-3E.

Figure 5A:
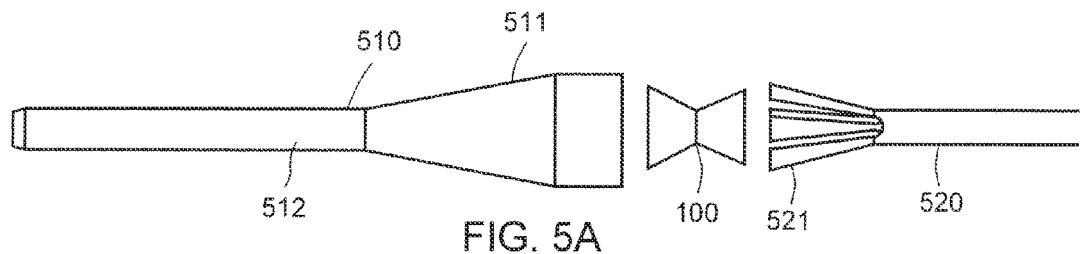
FIGS. 5A-5D schematically illustrate steps taken during the method of FIG. 4, according to some embodiments of the present invention.
Figure 5B:
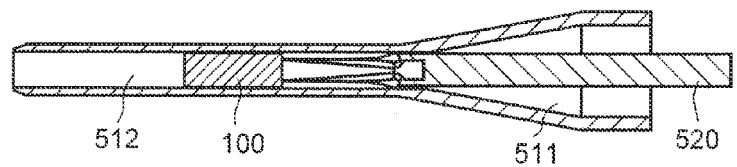

Then, the device is collapsed radially to a contracted delivery state, and loaded into a loading tube (step 402). For example, as illustrated in FIGS. 5A-5B, device 100 may be loaded into loading tube 510 using pusher 520 having "star"-shaped end 521. Loading tube 510 includes tapered loading end 511, which facilitates radial compression of device 100 into lumen 512 having a suitable internal diameter. Once device 100 is loaded into lumen 512, pusher 520 is retracted. Preferably, device 100 is loaded into loading tube 510 shortly before implantation, so as to avoid unnecessarily compressing device 100 or re-setting of the closed shape of leaflets 132, which may interfere with later deployment or operation of the device. In some embodiments, loading tube 510 has a diameter of 16 F or less, or 14 F or less, or 10 F or less, or 6 F or less, e.g., about 5 F, and device 100 has a crimped diameter of 16 F or less, or 14 F or less, or 10 F or less, or 6 F or less, e.g., about 5 F. In one illustrative embodiment, loading tube has a diameter of 15 F and device 100 has a crimped diameter of 14 F.

Figure 5C:
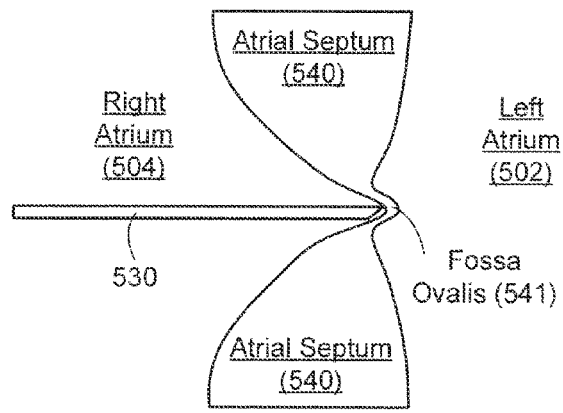

Referring again to FIG. 4, the device then is implanted, first by identifying the fossa ovalis of the heart septum, across which device 100 is to be deployed (step 403). Specifically, a BROCKENBROUGH needle may be percutaneously introduced into the right atrium via the subject's venous vasculature, for example, via the femoral artery. Then, under fluoroscopic or echocardiographic visualization, the needle is pressed against the fossa ovalis, at a pressure insufficient to puncture the fossa ovalis. As illustrated in FIG. 5C, the pressure from needle 530 causes "tenting" of fossa ovalis 541, i.e., causes the fossa ovalis to stretch into the left atrium. Other portions of atrial septum 540 are thick and muscular, and so do not stretch to the same extent as the fossa ovalis. Thus, by visualizing the extent to which different portions of the atrial septum 540 tents under pressure from needle 530, fossa ovalis 541 may be identified, and in particular the central portion of fossa ovalis 541 may be located.

Referring again to FIG. 4, the fossa ovalis (particularly its central region) may be punctured with the BROCKENBROUGH needle, and a guidewire may be inserted through the puncture by threading the guidewire through the needle and then removing the needle (step 404, not illustrated in FIG. 5). The puncture through the fossa ovalis then may be expanded by advancing a dilator over the guidewire. Alternatively, a dilator may be advanced over the BROCKENBROUGH needle, without the need for a guidewire. The dilator is used to further dilate the puncture and a sheath then is advanced over the dilator and through the fossa ovalis; the dilator and guidewire or needle then are removed (step 405, not illustrated in FIG. 5). The loading tube, with device 100 disposed in a contracted delivery state therein, then is advanced into the sheath (step 406, not illustrated in FIG. 5).

Figure 5D:
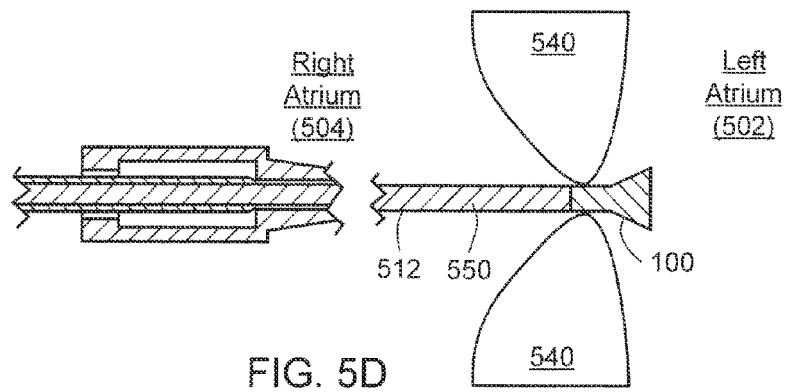

The device then is advanced out of the loading tube and into the sheath using a pusher, and then partially advanced out of the sheath, such that the second flared end of the device protrudes out of the sheath and into the left atrium, and expands to its deployed state (step 407). For example, as illustrated in FIG. 5D, pusher 550 may be used to partially advance device 100 out of sheath 512 and into left atrium 502, which causes the second flared end region to expand in the left atrium. The pusher may be configured such that it cannot advance the device 100 completely out of the sheath, but instead may only push out the side of the device to be disposed in the left atrium, that is, the second flared end region. After the pusher advances the second flared end region out of the sheath, the pusher may be mechanically locked from advancing the device out any further. For example, an expanded region may be disposed on the end of the pusher proximal to the physician that abuts the sheath and prevents further advancement of the pusher after the second flared end region is advanced out of the sheath. The device then may be fully deployed by pulling the sheath back, causing the second flared end region of the device to engage the left side of the atrial septum. Such a feature may prevent accidentally deploying the entire device in the left atrium.

The sheath then is retracted, causing the second flared end region to flank the left side of the atrial septum and the neck of the device to lodge in the puncture through the fossa ovalis, and allowing expansion of the first flared end of the device into the right atrium (step 408, see also FIG. 2B). Any remaining components of the delivery system then may be removed, e.g., sheath, and loading tube (step 409). Once positioned in the fossa ovalis, the device shunts blood from the left atrium to the right atrium when the left atrial pressure exceeds the right atrial pressure (step 410), thus facilitating treatment and/or the amelioration of symptoms associated with CHF.

Figure 6A:
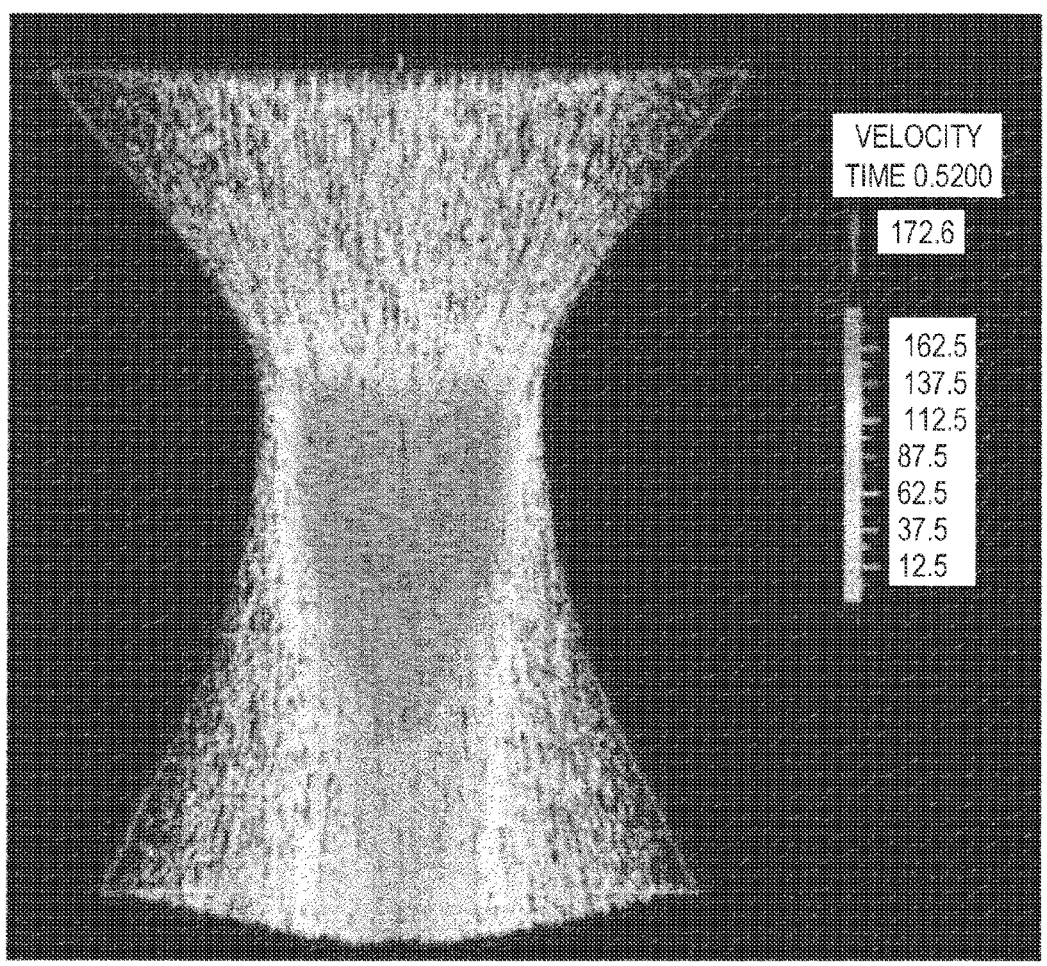
FIG. 6A is an image from a computational fluid dynamic model of flow through an hourglass-shaped device in the open configuration.

The performance characteristics of device 100 were characterized using computational fluid dynamic modeling. FIG. 6A is a cross-sectional image of fluid flow through device 100 in the open configuration, in which intensity indicates fluid velocity through the device. As can be seen in FIG. 6A, there are substantially no points of stagnation or turbulence in the blood flow. The maximum shear stresses within device 100 were calculated to be about 50-60 Pascal, which is significantly lower than values that may lead to thrombus formation, which are above 150 Pascal.

Figure 6B:
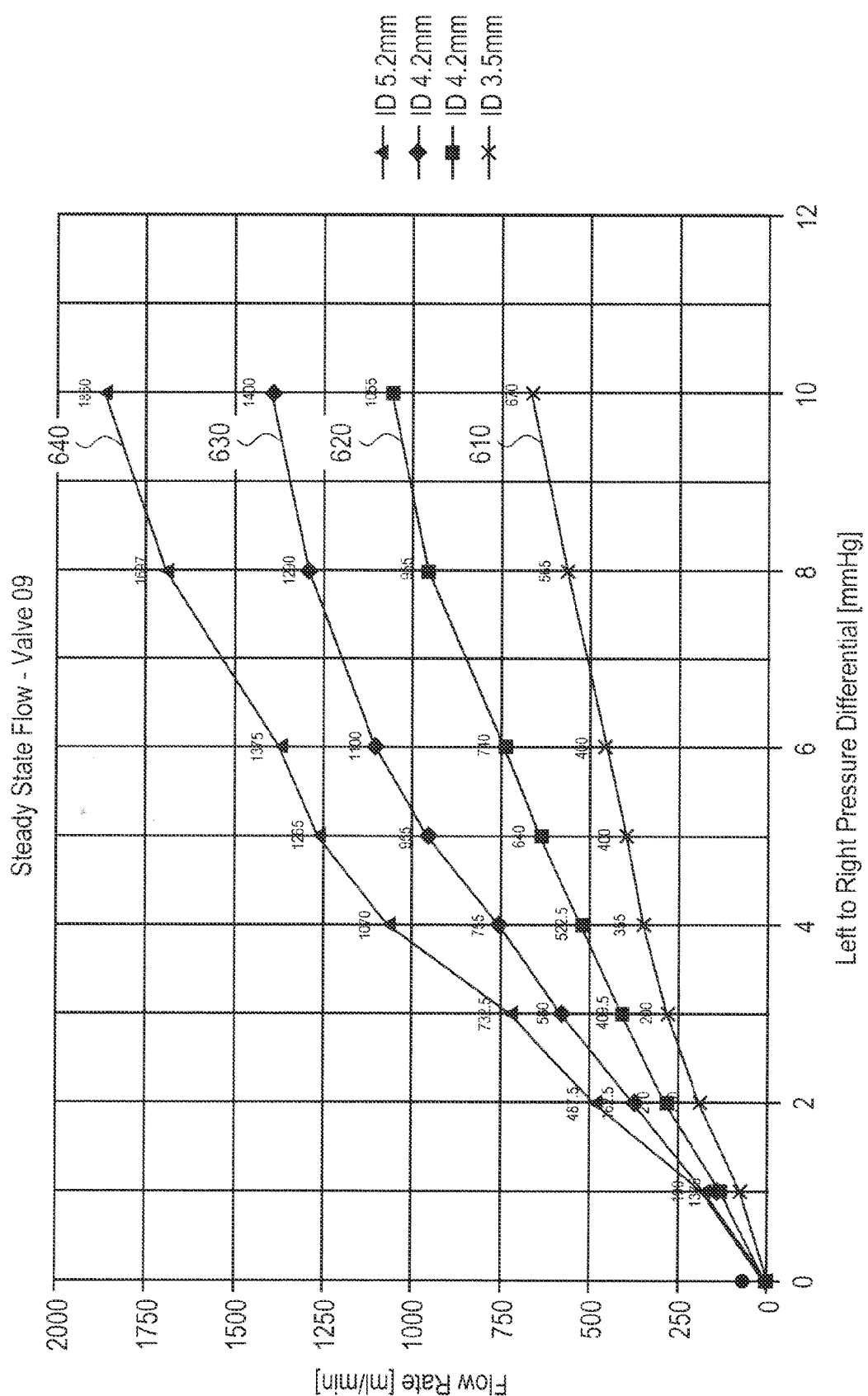
FIG. 6B is a plot showing the relationship between the left-to-right atrial pressure differential and the flow rate through the valve for hourglass-shaped devices having different valve diameters, according to some embodiments of the present invention.

The performance of device 100 was also characterized using hemodynamic testing. FIG. 6B is a plot of the flow rate through device 100 as a function of the pressure differential between the left and right atria, for devices having inner diameters of 3.5 mm (trace 610), 4.2 mm (trace 620), 4.8 mm (trace 630), and 5.2 mm (trace 640). At a pressure differential of 10 mm Hg, it can be seen that the flow rate of the 3.5 mm device was 670 ml/minute; the flow rate of the 4.2 mm device was 1055 ml/minute; the flow rate of the 4.8 mm device was 1400 ml/minute; and the flow rate of the 5.2 mm device was 1860 ml/minute. Based on these measurements, it is believed that devices having inner diameters of 4.5 mm to 4.8 mm may provide suitable flow parameters over time, when implanted, because ingrowth of septal tissue over the first 6 months following implantation may reduce the inner diameter to about 3.5 to 3.8 mm, thus reducing the flow rate to below about 800 ml/minute. At steady state, such a flow rate may reduce the left atrial pressure by 5 mmHg, to around 10-15 mmHg, and may reduce the pressure differential between the left and right atria to about 4-6 mmHg.

Additionally, device 100 was subjected to an accelerated wear and fatigue test for up to 100 million cycles to simulate and predict fatigue durability, and was observed to perform satisfactorily.

The devices and methods described herein may be used to regulate left atrial pressures in patients having a variety of disorders, including congestive heart failure (CHF), as well as other disorders such as patent foramen ovale (PFO), or atrial septal defect (ASD). The devices and methods also may be used to reduce symptoms and complications associated with such disorders, including myocardial infarction. It is believed that patients receiving the device may benefit from better exercise tolerance, less incidence of hospitalization due to acute episodes of heart failure, and reduced mortality rates.

Figure 7:
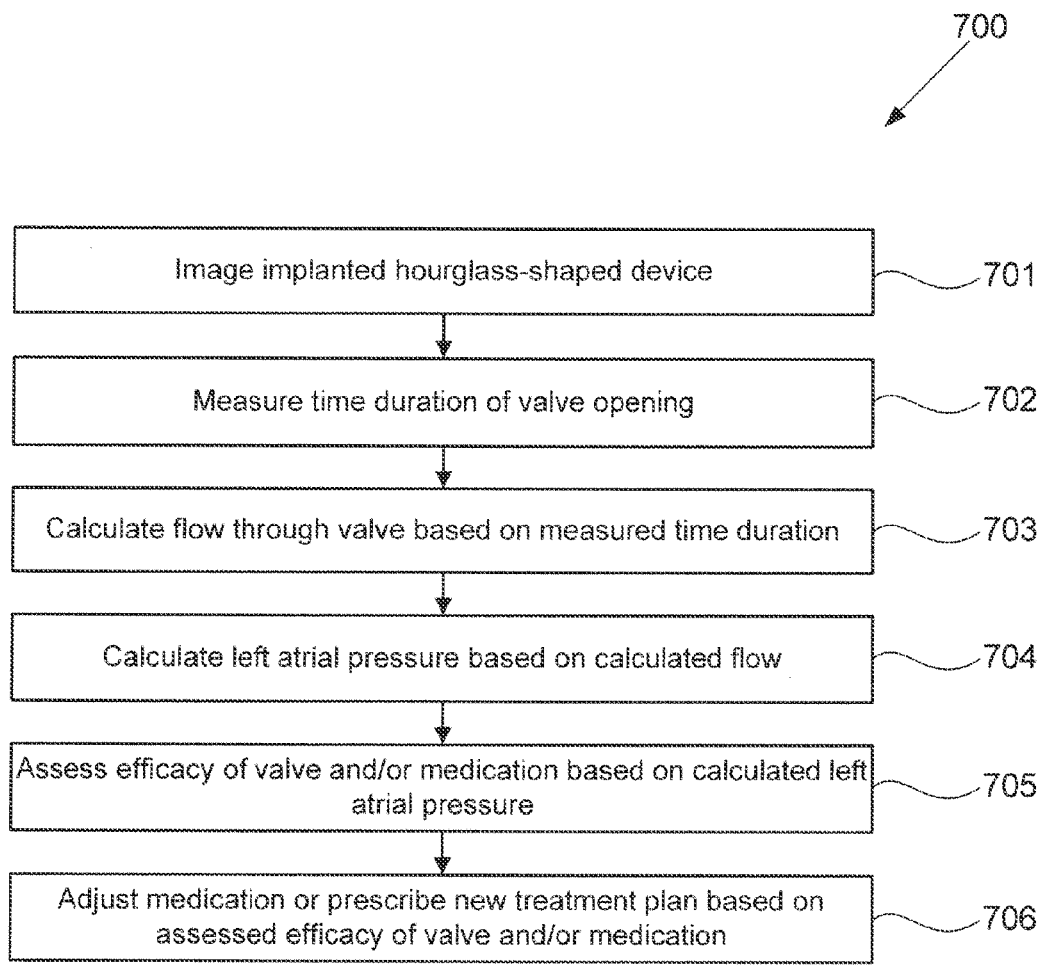
FIG. 7 is a flow chart of steps in a method of noninvasively determining left atrial pressure using an hourglass-shaped device, and adjusting a treatment plan based on same, according to some embodiments of the present invention.

The devices and methods described herein further may be used to non-invasively determine the pressure in the left atrium, and thus to assess the efficacy of the device and/or of any medications being administered to the patient. Specifically, with respect to FIG. 7, method 700 includes imaging an implanted hourglass-shaped device, e.g., device 100 described above with respect to FIGS. 1A-1D (step 701). Such imaging may be ultrasonic, e.g., cardioechographic, or may be fluoroscopic. Using such imaging, the time duration of the opening of tissue valve 130 may be measured (step 702). Based on the measured time duration, the flow of blood through the valve may be calculated (step 703). The left atrial pressure then may be calculated based on the calculated flow, for example, based on a curve such as shown in FIG. 6B (step 704). Based on the calculated left atrial pressure, the efficacy of the valve and/or of any medication may be assessed (step 705). A physician may adjust the medication and/or may prescribe a new treatment plan based on the assessed efficacy of the valve and/or the medication.

Some alternative embodiments of device 100 described above with respect to FIGS. 1A-1D are now described. In particular, tissue valves other than tricuspid valve 130 illustrated above with respect to FIGS. 1A-1D may be employed with device 100. For example, device 800 illustrated in FIGS. 8A-8C includes hourglass-shaped stent 110, which may be substantially the same as stent 110 described above, biocompatible material 120, and duckbill tissue valve 830. Like device 100, device 800 has three general regions: first flared or funnel-shaped end region 102 configured to flank the right side of the atrial septum, second flared or funnel-shaped end region 106 configured to flank the left side of the atrial septum, and neck region 104 disposed between the first and second flared end regions and configured to lodge in a puncture formed in the atrial septum, preferably in the fossa ovalis. Stent 110 includes plurality of sinusoidal rings 112-116 interconnected by longitudinally extending struts 111, which may be laser cut from a tube of shape memory metal. Neck region 104 and second flared end region 106 may be covered with biocompatible material 120, e.g., in the region extending approximately from sinusoidal ring 113 to sinusoidal ring 116.

Duckbill tissue valve 830 is coupled to stent 110 in first flared end region 102. Preferably, tissue valve 830 opens at a pressure of less than 1 mmHg, closes at a pressure gradient of 0 mmHg, and remains closed at relatively high back pressures, for example at back pressures of at least 40 mmHg. Like tissue valve 130, tissue valve 830 may be formed using any natural or synthetic biocompatible material, including but not limited to pericardial tissue, e.g., thinned and fixed bovine, equine, or porcine pericardial tissue. As shown in FIG. 8B, the outlet of duckbill tissue valve 830 is coupled, e.g., sutured, to first and second longitudinally extending struts 111', 111" in the region extending between first (uppermost) sinusoidal ring 112 and second sinusoidal ring 113. Referring again to FIG. 8A, the inlet to tissue valve 830 also is coupled, e.g., sutured, to the upper edge of the biocompatible material 120 along line 121, at or near sinusoidal ring 113, so as to provide a smooth profile.

Figure 8A:
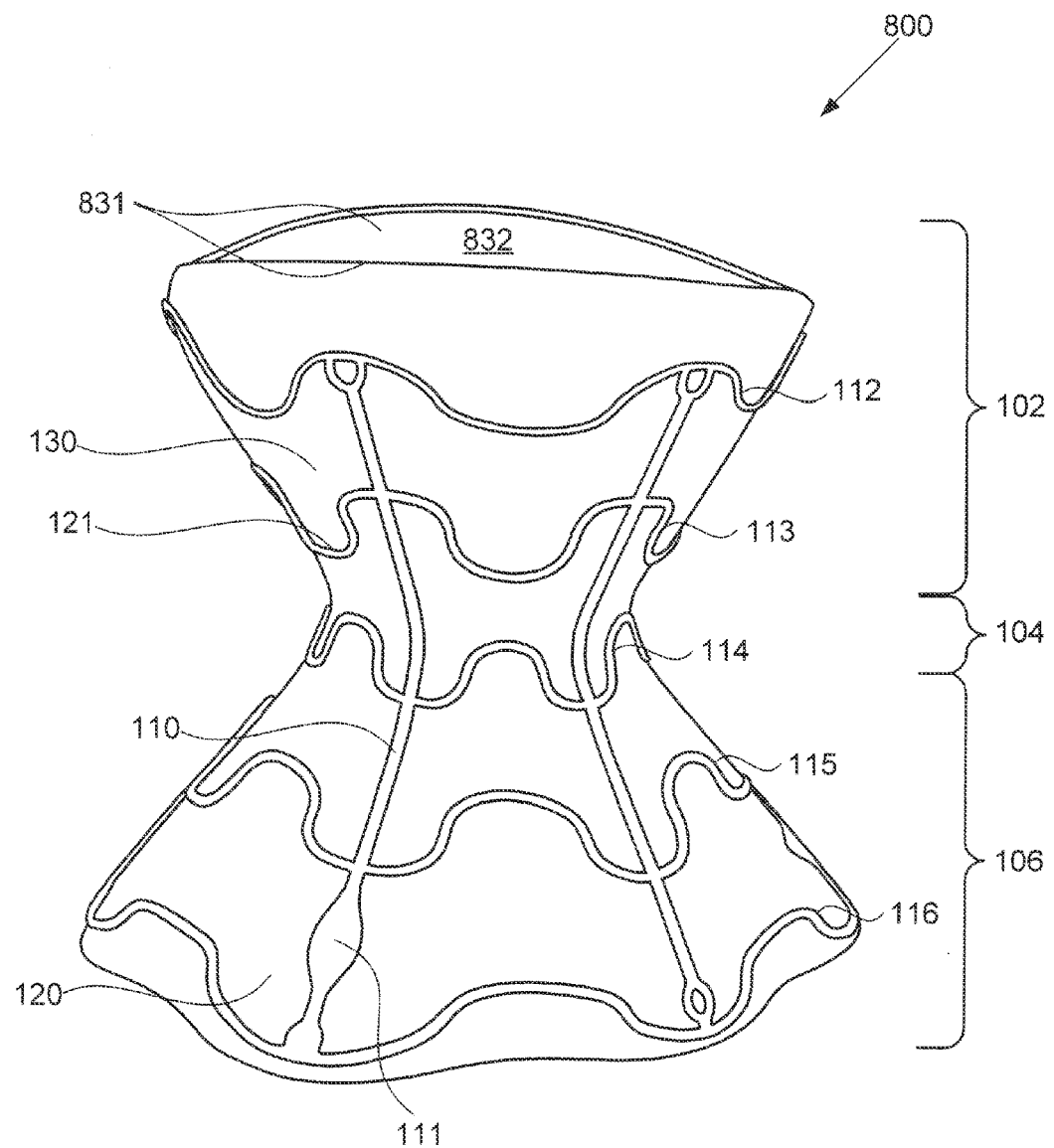
FIGS. 8A-8C illustrate perspective views of an alternative hourglass-shaped device, according to some embodiments of the present invention.
Figure 8B:
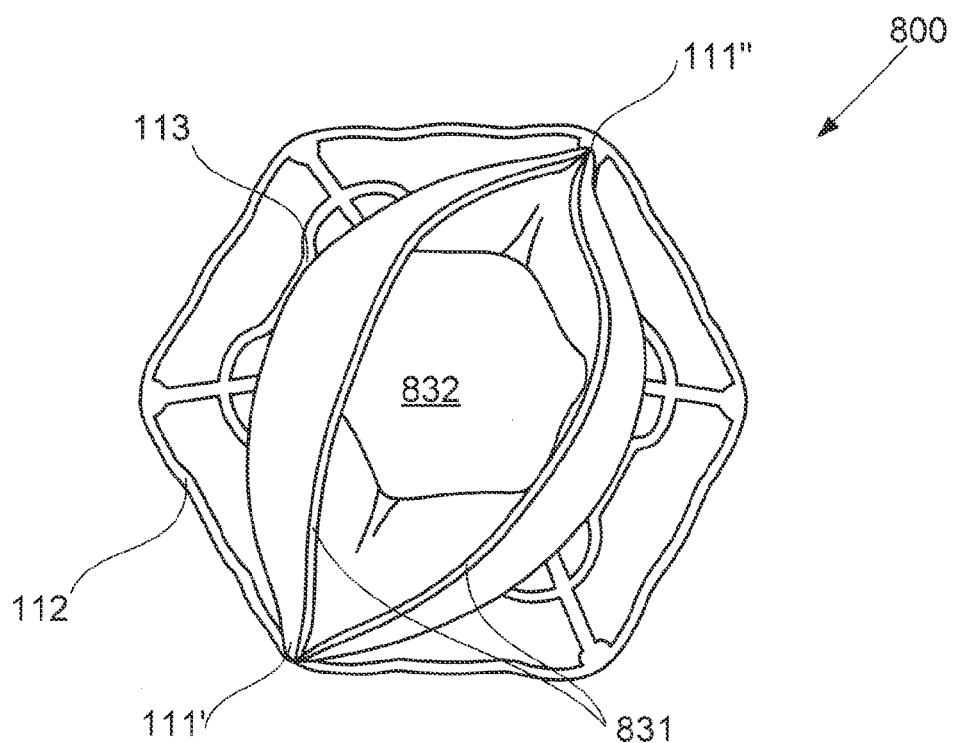
Figure 8C:
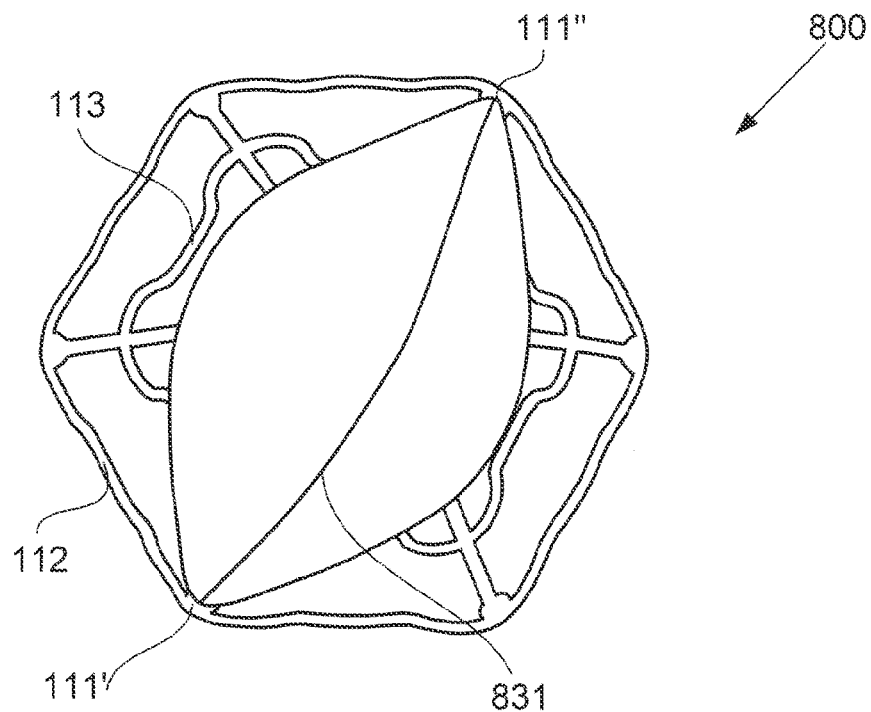

FIGS. 8A and 8B illustrate device 800 when duckbill tissue valve 830 is in an open configuration, in which leaflets 931 are in an open position to permit flow. FIG. 8C illustrates device 800 when tissue valve 830 is in a closed configuration, in which leaflets 831 are in a closed position to inhibit flow, in which position they preferably form a substantially straight line. Device 800 preferably is configured so as to provide flow characteristics similar to those described above for device 100.

Figure 9:
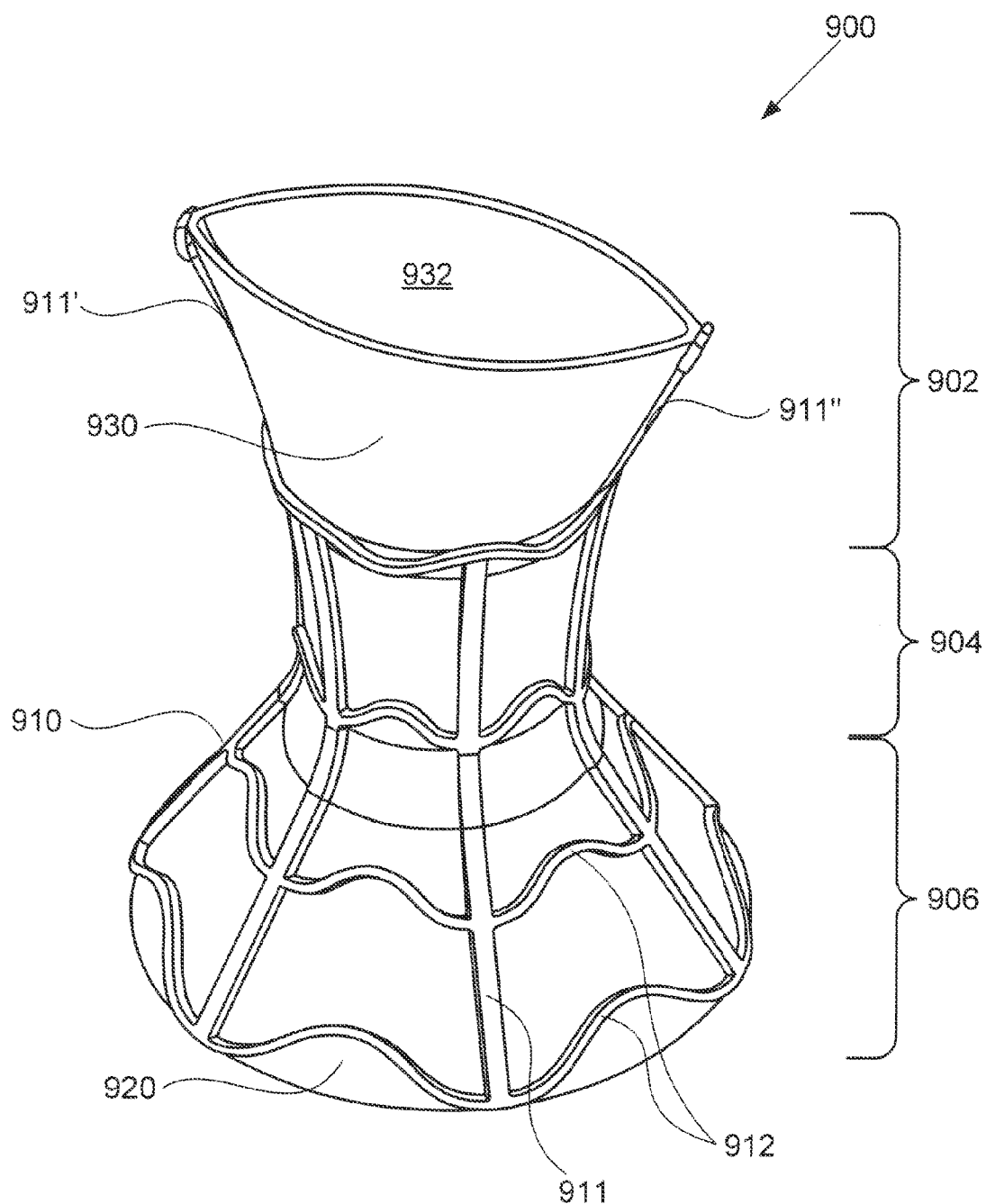
FIG. 9 is a perspective view of a further alternative hourglass-shaped device, according to some embodiments of the present invention.

Referring now to FIG. 9, alternative device of the present invention is described. Device 900 has first and second flared end regions 902, 906, with neck region 904 disposed therebetween. Device 900 includes hourglass-shaped stent 910, biocompatible material 920, and tissue valve 930 and further comprises three general regions as described for the foregoing embodiments: first flared or funnel-shaped end region 902 configured to flank the right side of the atrial septum, second flared or funnel-shaped end region 906 configured to flank the left side of the atrial septum, and neck region 904 disposed between the first and second flared end regions and configured to lodge in a puncture formed in the atrial septum, preferably in the fossa ovalis. Like the devices described above, stent 910 includes plurality of sinusoidal rings 912 interconnected by longitudinally extending struts 911, which may be laser cut from a tube of shape memory metal. However, as compared to devices 100 and 800 described further above, sinusoidal rings 912 do not extend into first flared end region 902. Instead, the outlet end of tissue valve 930 is coupled to longitudinally extending struts 911' and 911". Neck region 904 and second flared end region 906 may be covered with biocompatible material 920.

Duckbill tissue valve 930 is coupled to stent 910 in first flared end region 902. Specifically, the outlet of tissue valve 930 is coupled, e.g., sutured, to first and second longitudinally extending struts 911', 911" in the region extending between the first (uppermost) sinusoidal ring 912 and the distal ends of struts 911', 911". The inlet end of tissue valve 930 also is coupled, e.g., sutured, to the upper edge of biocompatible material 920 at or near first (uppermost) sinusoidal ring 912, so as to provide a smooth profile. Device 900 is preferably configured so as to provide flow characteristics similar to those described above for device 100.

EXAMPLE

An exemplary device 800 such as described above with respect to FIGS. 8A-8C was implanted into four sheep with induced chronic heart failure (V1-V4), while four sheep with induced chronic heart failure did not receive the device, and were used as a control (C1-C4). An additional control animal was subjected to only a partial heart failure protocol, and did not receive the device (S1).

Chronic heart failure was induced in animals C1-C4 and V1-V4, who were less than 1 year of age and weighed between 70 and 120 pounds, by first anesthetizing the animals via a venous catheter positioned in a peripheral vessel, i.e., the ear. The animals were given an opiate or synthetic opiate (e.g., morphine or butorphanol) intravenously at 0.25 to 0.5 mg/kg, as well as telazol at 0.3 mg/kg, through the venous catheter, and anesthetized by intravenous etomidate. Anesthesia was maintained with 1.5% isoflurane delivered in 100% $O_2$, via a tracheal tube. The animals were placed on a fluoroscope table in left lateral recumbence, and a gastric tube (about 7 F) was inserted into the rumen to serve as a vent.

An introducer was then positioned within the carotid artery via cut down and modified Seldinger technique. A 6 F or 7 F Judkins left 4.5 catheter was advanced through the introducer into the left circumflex coronary artery (LCxA) under fluoroscopic guidance, and about 60,000 polystyrene microspheres of about 90 μm diameter were injected into the LCxA to induce embolization to induce myocardial infarction followed by chronic heart failure. The arterial and skin incisions then were closed, and the animals were administered about 500 mg of cephalexein p.o. bid for two days, as well as a synthetic opiate prn, specifically buprenorphine administered intramuscularly at about 0.03 to 0.05 mg/kg, once during recovery and following the anesthesia. Animals observed to have arrhythmia following or during the microsphere injection were also administered lidocaine following embolization, at about 2 to 4 mg/kg via intravenous bolus, followed by constant infusion at about 20 to 80 μf/kf/minute.

This procedure was repeated one week following the first procedure in animals V1-V4 and C1-C4. This model of induced chronic heart failure has about a 100% fatality rate at 12 weeks, and as discussed below each of the control animals died before the end of the 12 week study. The procedure was performed a single time in animal S1, and as discussed below this animal survived the 12 week study but deteriorated over the course of the study.

Device 800 was implanted into four animals V1-V4. Fluid filled catheters were implanted into animals V1-V4 and C1-C4, approximately seven days after the second embolization procedure. Fluid filled catheters were not implanted into animal S1. The implanted device 800 had an overall length of 15 mm (7 mm on the left atrial side and 8 mm on the right atrial side), a diameter on the left atrial side of 14 mm, a diameter on the right atrial side of 13 mm, an inside neck diameter of 5.3 mm, and an angle between the left and right atrial sides of the device of 70 degrees. The fluid filled catheters were implanted in the inferior vena cava (IVC), superior vena cava (SVC), pulmonary artery, and left atrium through a right mini-thoracotomy under anesthesia, and were configured to measure oxygen saturations and pressures in the IVC, pulmonary artery, right atrium, and left atrium. After implantation and throughout the study, the animals were each treated daily with aspirin, plavix, and clopidogrel. Their heart rate was periodically monitored.

Two-dimensional M-mode echocardiograms of the left ventricle were periodically obtained to document the ejection fraction (EF), as well as the shortening fraction, calculated as 100(EDD−ESD)/EDD, where EDD is the end-diastolic dimension (diameter across ventricle at the end of diastole) and ESD is the end-systolic dimension (diameter across ventricle at the end of systole). Echocardiographic studies of the animals were performed while they were either conscious or under light chemical restraint with butorphanol, and manually restrained in the right or left decubitis position, using an ultrasound system with a 3.5 to 5.0 mHz transducer (Megas ES, model 7038 echocardiography unit). The echocardiograms were recorded for subsequent analysis. The left ventricle fractional area shortening (FAS), a measure of left ventricle systolic function, was measured from the short axis view at the level of the papillary muscles. Measurements of left ventricle dimensions, thickness of the posterior wall, and intraventricular septum were obtained and used as an index of left ventricle remodeling. The major and minor axes of the left ventricle were measured and used to estimate left ventricle end-diastolic circumferential wall stress.

The clinical conditions of the animals were evaluated by comparing various parameters over a twelve-week period, including left atrial pressure, right atrial pressure, pulmonary artery pressure, and ejection fraction (EF). Parameters such as left and right atrial pressures, left and right ventricular dimensions, and left and right ventricular function were obtained based on the collected data. Data obtained during the study are discussed further below with respect to FIGS. 10A-10D and Tables 2-15.

During the course of the study, all four of the control animals C1-C4 were observed to suffer from high pulmonary artery pressure, high right atrial pressure, and low ejection fraction, and were immobile. All four control animals died during the trial, C3 at week 1, C4 at week 3, C1 at week 6, and C2 at week 9. Animal S1 survived but deteriorated over the course of the study.

By comparison, all of the animals V1-V4 into which the device had been implanted were observed to have dramatically improved hemodynamic conditions over the course of the study, and appeared healthy and energetic without signs of congestion by the end of the study. As discussed below with reference to FIGS. 10A-10D, device 800 was observed to reduce left atrial pressure in the implanted animals by about 5 mmHg, with an increase in cardiac output, and preservation of right atrial pressure and pulmonary artery pressure. Left ventricle parameters were observed to be substantially improved in the implanted animals as compared to the control animals, and right ventricle and pulmonary artery pressure were also observed to be normal in the implanted animals.

Three of the four implanted animals, V1, V3, and V4 survived the twelve week study. One of the implanted animals, V2, died at week 10 of a non-heart failure cause. Specifically, arrhythmia was diagnosed as the cause of death; the animal was observed to have arrhythmia at baseline, and had been defibrillated before implantation. Throughout the study, this animal was observed to have good hemodynamic data. At the end of the study, the surviving implant animals were observed to respond normally to doses of dobutamine, indicating significant improvement in the condition of their heart failure.

Figure 10A:
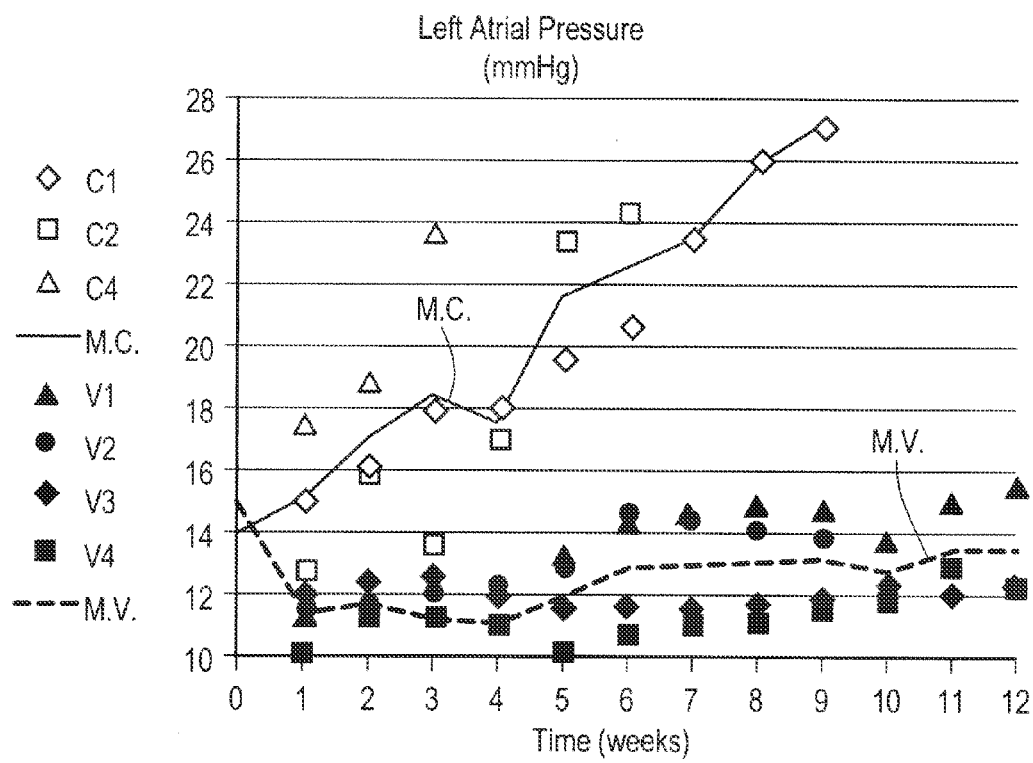
FIGS. 10A-10D are plots respectively showing the left atrial pressure, right atrial pressure, ejection fraction, and pulmonary artery pressure in animals into which an exemplary hourglass-shaped device was implanted, as well as control animals, during a twelve-week study.

FIG. 10A is a plot of the measured left atrial pressure of the control animals (C1-C4), and of the implanted animals (V1-V4), along with mean values for each (M.C. and M.V., respectively). Data for control animal C3 is not shown, as the animal died in the first week of the study. The mean left atrial pressure for the control animals (M.C.) was observed to steadily increase over the course of the study, from about 14 mmHg at baseline to over 27 mmHg when the last control animal (C1) died. By comparison, the mean left atrial pressure for the implanted animals (M.V.) was observed to drop from about 15 mmHg at baseline to less than 12 mmHg at week one, and to remain below 14 mmHg throughout the study.

Figure 10B:
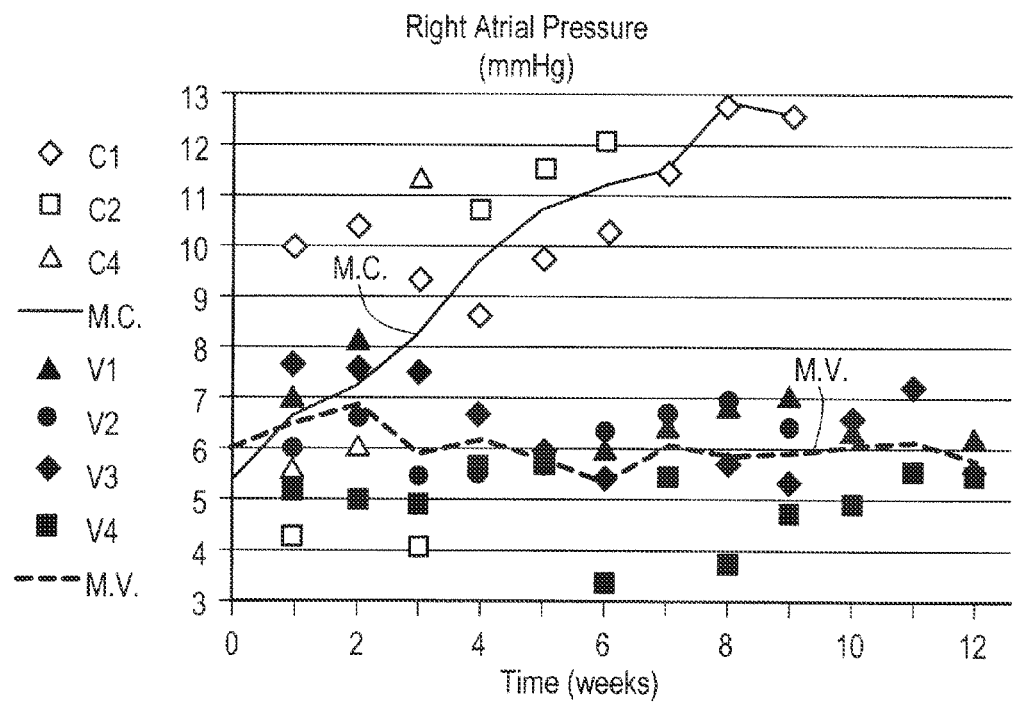

FIG. 10B is a plot of the measured right atrial pressure of the control animals (C1-C4), and of the implanted animals (V1-V4), along with mean values for each (M.C. and M.V., respectively). Data for control animal C3 is not shown. As for the left atrial pressure, the mean right atrial pressure for the control animals (M.C.) was observed to steadily increase over the course of the study, from about 5.5 mmHg at baseline to over 12 mmHg when the last control animal (C1) died. By comparison, the mean right atrial pressure for the implanted animals (M.V.) was observed to remain relatively steady throughout the study, increasing from about 6 mmHg to about 7 mm Hg over the first two weeks of the study, and then decreasing again to about 6 mmHg for the rest of the study.

Figure 10C:
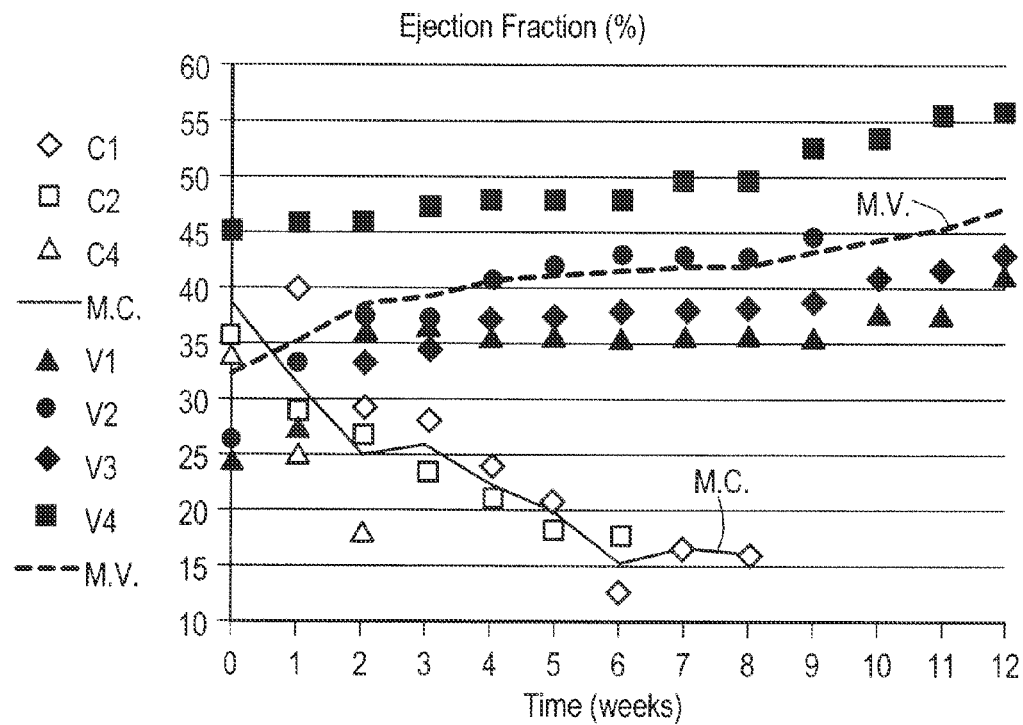

FIG. 10C is a plot of the measured ejection fraction of the control animals (C1-C4), and of the implanted animals (V1-V4), along with mean values for each (M.C. and M.V., respectively). Data for control animal C3 is not shown. The mean ejection fraction for the control animals (M.C.) was observed to steadily decrease over the course of the study, from about 38% at baseline to about 16% when the last control animal (C1) died. By comparison, the mean ejection fraction for the implanted animals (M.V.) was observed to steadily increase over the course of the study, from about 33% at baseline to about 46% at the conclusion of the study.

Figure 10D:
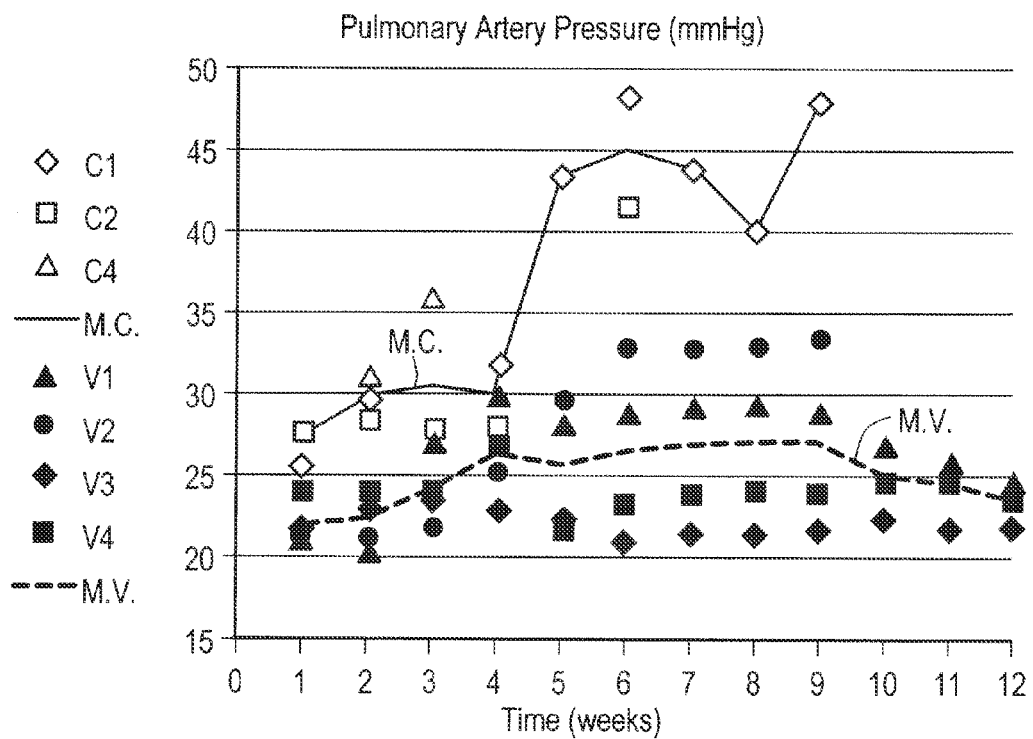

FIG. 10D is a plot of the measured pulmonary artery pressure of the control animals (C1-C4), and of the implanted animals (V1-V4), along with mean values for each (M.C. and M.V., respectively). Data for control animal C3 is not shown. The mean pulmonary artery pressure for the control animals (M.C.) was observed to vary significantly over the course of the study, from about 27 mmHg during the first week of the study, to about 45 mmHg at week six, then down to 40 mmHg at week eight, and then up to about 47 mmHg at week nine, when the last control animal (C1) died. By comparison, the mean pulmonary artery pressure for the implanted animals (M.V.) was observed to remain relatively steady, increasing from about 22 mmHg during week one, to about 27 mmHg during weeks four through nine, and then back down to about 24 mmHg by week twelve, at the conclusion of the study.

Figure 11A:
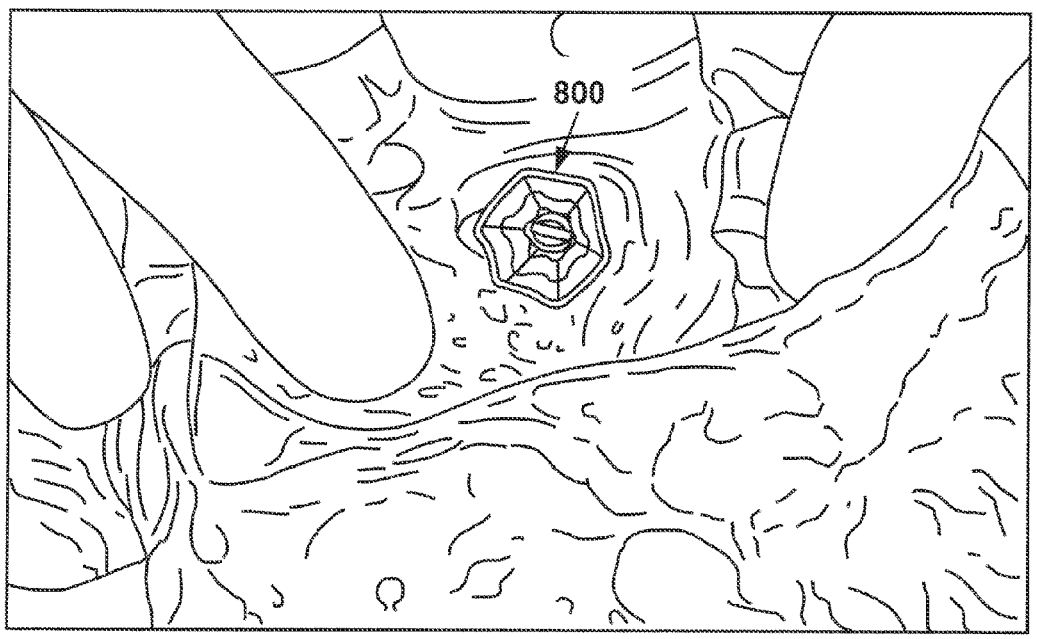
FIGS. 11A-11B are photographic images showing an hourglass-shaped device following explantation from an animal after being implanted for 12 weeks.
Figure 11B:
Figure 11C:
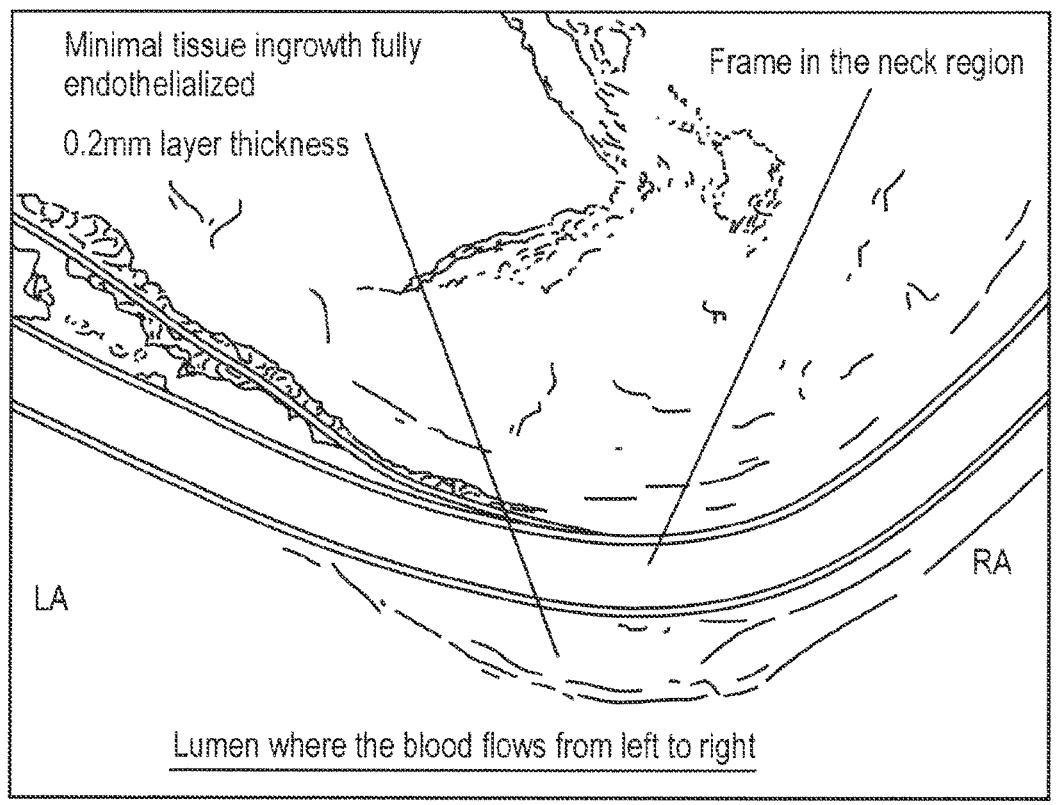
FIG. 11C is a microscope image of a cross-section of an hourglass-shaped device following explantation from an animal after being implanted for 12 weeks.

Upon explantation at the end of the study, three of the four implanted devices were observed to be completely patent and functional. For example, FIGS. 11A-11B are photographic images of device 800 upon explantation from one of the implanted animals, taken from the left atrial and right atrial sides respectively. A fourth device was observed to be patent up until week 11, using Fick's measurements and echocardiography. At histopathology, no inflammation was observed around the valves, and a thin endothelial layer was observed to have ingrown. For example, FIG. 11C is a microscope image of device 800 upon explantation from one of the implanted animals, showing approximately 0.2 mm of endothelial tissue in the device in the neck region.

Tables 2 through 15 present raw data obtained from the control animals C1-C4 and S1 and the implanted animals V1-V4, while awake, over the course of the 12 week study, including baseline immediately before implantation (Day 0, during which the animals were sedated). The mean values for control animals C1-C4 and S1 (M.C.) and the mean values for the implanted animals V1-V4 (M.V.), with standard deviations, are also presented in the tables. Missing data indicates either the death of the animal or omission to obtain data. Data for animal C3 is not shown because the animal died in the first week of the study. Data was not collected for any animal in week 7 of the study. As noted above, animal S1 was not implanted with pressure and saturation flow monitors, so no data is shown for that animal for certain measurements.

Table 2 presents the study's results pertaining to right atrial pressure (RAP, mmHg). As can be seen from Table 2, the average RAP for the control animals (C1-C4) increased significantly over the course of the study. For example, animal C1 experienced an RAP increase to about 330% of baseline before death, C2 to about 110% of baseline before death, and C4 to about 340% of baseline before death. The increase was relatively steady during this period. By contrast, the RAP for the implanted animals (V1-V4) started at a similar value to that of the control animals, at an average of 6±2 mmHg at baseline, but did not significantly vary over the course of the study. Instead, the average RAP of the implanted animals remained within about 1-2 mmHg of the baseline value for the entire study (between a high of 7±1 and a low of 5±1). Thus, the inventive device may inhibit increases in the right atrial pressure in subjects suffering from heart failure, and indeed may maintain the right atrial pressure at or near a baseline value. This is particularly noteworthy because, as described elsewhere herein, the device may offload a relatively large volume of blood from the left atrium to the right atrium; however the relatively high compliance of the right atrium inhibits such offloading from significantly increasing RAP.

TABLE 2

Right Atrial Pressure (RAP, mmHg)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   | 3.8   | 4.3   | 5.1   | 4.1   | 10.8  | 11.6  | 12.1  | 12.8  | 12.6  |        |        |        |
| C2   | 9.2   | 10.1  | 10.5  | 9.8   | 8.6   | 9.8   | 10.3  |       |       |        |        |        |
| C4   | 3.3   | 5.7   | 6.1   | 11.4  |       |       |       |       |       |        |        |        |
| S1   |       |       |       |       |       |       |       |       |       |        |        |        |
| V1   | 8.9   | 7.1   | 8.2   | 5.6   | 6.8   | 5.7   | 6.1   | 6.9   | 7.1   | 6.5    | 5.7    | 6.3    |
| V2   | 7.4   | 6.1   | 6.7   | 5.5   | 5.6   | 6.0   | 6.4   | 7.0   | 6.5   |        |        |        |
| V3   | 8.0   | 7.7   | 7.7   | 7.6   | 6.7   | 6.0   | 5.5   | 5.8   | 5.4   | 6.7    | 7.2    | 5.7    |
| V4   | 0.9   | 5.2   | 5.1   | 4.9   | 5.7   | 5.8   | 3.4   | 3.8   | 4.8   | 5.0    | 5.6    | 5.7    |
| M.C. | 5 ± 2 | 7 ± 2 | 7 ± 1 | 8 ± 2 | 10 ± 1| 11 ± 1| 11 ± 1| 13    | 13    |        |        |        |
| M.V. | 6 ± 2 | 7 ± 1 | 7 ± 1 | 6 ± 1 | 6 ± 0 | 6 ± 0 | 5 ± 1 | 6 ± 1 | 6 ± 1 | 6 ± 1  | 6 ± 1  | 6 ± 0  |

Table 3 presents the study's results pertaining to left atrial pressure (LAP, mmHg). As can be seen from Table 3, the average LAP of the control animals started at a similar value at baseline as that of the implanted animals, 14±1 mmHg for the former and 15±2 mmHg for the latter. However, the LAP of the control animals increased significantly over the course of the study. For example, animal C1 had a baseline LAP of 10.6 mmHg, and an LAP of 27.3 mmHg at week 9 just before death, about 250% of baseline. The LAP increases of the other control animals were smaller, but still significantly larger than that of the implanted animals. Indeed, in each case the LAP of the implanted animals actually decreased immediately following implantation. For example, the LAP for animal V1 decreased from 15.7 mmHg at baseline to 11.4 mmHg one week following implantation, about 73% of baseline. The average LAP for the implanted animals decreased from 15±2 at baseline to a low of 11±0 at week one, and then gradually increased to about 13±1 at week six (about 87% of baseline), where it remained for the remainder of the study.

Table 4 further elaborates the results presented in Table 3, and presents the calculated change in LAP (ΔLAP, %). As can be seen in Table 4, control animals C2 and C4 each died after their LAP increased by about 44%, while control animal C1 died after its LAP increased by about 158%. By comparison, implanted animals V1, V2, and V3 each experienced significant decreases in LAP immediately following implantation, e.g., by about −27%, −41%, and −15% relative to baseline. The LAP for animal V4 remained near baseline following implantation. The LAP for animal V1 slowly increased back to baseline over the course of the study; the LAP for animal V2 remained significantly below baseline before its death but increased somewhat; the LAP for animal V3 also remained below baseline throughout the study but increased somewhat; and the LAP for animal V4 fluctuated somewhat above baseline but remained within about 18% of baseline. Thus, it can be seen that the inventive device may inhibit increases in the left atrial pressure in patients suffering from heart failure. Indeed, the device may actually decrease the left atrial pressure below baseline in patients suffering from heart failure for a time period immediately following implantation, in some embodiments to a level about 20% below baseline. The left atrial pressure subsequently may gradually increase back towards a baseline level over a time period of weeks or months, as the heart remodels and improves in efficiency. It is important to note that the control animals died from pulmonary edema, which correlates with LAPs that exceed the "danger zone" of 25 mmHg or more at which edema occurs.

TABLE 3

Left Atrial Pressure (LAP, mmHg)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   | 10.6  | 12.8  | 15.9  | 13.6  | 17.0  | 23.5  | 24.4  | 26.0  | 27.3  |        |        |        |
| C2   | 14.4  | 15.1  | 16.3  | 18.1  | 18.1  | 19.7  | 20.7  |       |       |        |        |        |
| C4   | 16.4  | 17.7  | 18.9  | 23.7  |       |       |       |       |       |        |        |        |
| S1   |       |       |       |       |       |       |       |       |       |        |        |        |
| V1   | 15.7  | 11.4  | 11.3  | 8.8   | 9.2   | 13.4  | 14.3  | 15.0  | 14.9  | 13.9   | 15.2   | 15.6   |
| V2   | 19.8  | 11.7  | 11.7  | 12.1  | 12.3  | 13.0  | 14.7  | 14.2  | 14.0  |        |        |        |
| V3   | 14.3  | 12.1  | 12.4  | 12.7  | 12.0  | 11.5  | 11.6  | 11.8  | 11.9  | 12.4   | 13.0   | 12.3   |
| V4   | 10.3  | 10.1  | 11.3  | 11.4  | 11.0  | 10.2  | 10.8  | 11.2  | 11.7  | 11.9   | 12.2   | 12.1   |
| M.C. | 14 ± 1| 15 ± 1| 17 ± 1| 1     | 18 ± 0| 22 ± 2| 23 ± 2| 26    | 27    |        |        |        |
| M.V. | 15 ± 2| 11 ± 0| 12 ± 0| 11 ± 1| 11 ± 1| 12 ± 1| 13 ± 1| 13 ± 1| 13 ± 1| 13 ± 1 | 13 ± 1 | 13 ± 1 |

TABLE 4

Change in Left Atrial Pressure (ΔLAP, %)

|    | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|----|-------|-------|-------|-------|-------|-------|-------|-------|-------|--------|--------|--------|
| C1 |       | +5    | +51   | +29   | +61   | +122  | +131  | +145  | +158  |        |        |        |
| C2 |       | +21   | +14   | +26   | +26   | +37   | +44   |       |       |        |        |        |
| C4 |       | +8    | +15   | +44   |       |       |       |       |       |        |        |        |
| S1 |       |       |       |       |       |       |       |       |       |        |        |        |
| V1 |       | −27   | −28   | −44   | −41   | −15   | −9    | −4    | −5    | −11    | −3     | 0      |
| V2 |       | −41   | −41   | −39   | −38   | −34   | −26   | −28   | −29   |        |        |        |
| V3 |       | −15   | −13   | −11   | −16   | −20   | −19   | −17   | −16   | −13    | −9     | −13    |
| V4 |       | −2    | +10   | +10   | +7    | −1    | +5    | +8    | +13   | +16    | +18    | +17    |
| M.C. |     | +11 ± 4 | +27 ± 10 | +33 ± 5 | +44 ± 14 | +80 ± 42 | +87 ± 35 | +145 | +158 |  |  |  |
| M.V. |     | −21 ± 8 | −18 ± 11 | −21 ± 13 | −22 ± 11 | −17 ± 7 | −12 ± 7 | −10 ± 8 | −9 ± 9 | −3 ± 9 | +2 ± 8 | +1 ± 9 |

Table 5 presents the study's results pertaining to pulmonary artery pressure (PAP, mmHg). As can be seen in Table 5, the control animals experienced significant increases in PAP before death, e.g., about 230% of baseline for animal C1, 217% of baseline for animal C2, and 180% of baseline for animal C4. The PAP for the implanted animals also increased over the course of the study, but in most cases by significantly less than that of the control animals, e.g., to about 133% of baseline for animal V1, about 161% of baseline for animal V2, about 156% of baseline for animal V3, and about 169% for animal V4. The inventive device thus may inhibit increases in pulmonary artery pressure in subjects suffering from heart failure, relative to what they may otherwise have experienced during heart failure.

TABLE 5

Pulmonary Artery Pressure (PAP, mmHg)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   | 20.8  | 27.9  | 28.5  | 27.9  | 28.0  |       | 41.7  | 40.2  | 48.0  |        |        |        |
| C2   | 22.3  | 25.8  | 29.7  | 26.9  | 32.0  | 43.5  | 48.4  |       |       |        |        |        |
| C4   | 20.1  | 28.4  | 31.2  | 36.1  |       |       |       |       |       |        |        |        |
| S1   |       |       |       |       |       |       |       |       |       |        |        |        |
| V1   | 18.6  | 21.2  | 20.7  | 27.1  | 30.2  | 28.4  | 29.0  | 29.8  | 29.2  | 27.1   | 26.3   | 24.8   |
| V2   | 20.9  | 21.5  | 21.4  | 21.9  | 25.4  | 29.7  | 33.0  | 33.0  | 33.6  |        |        |        |
| V3   | 14.1  | 22.0  | 23.3  | 23.5  | 23.1  | 22.6  | 21.0  | 21.6  | 21.8  | 22.6   | 22.0   | 22.0   |
| V4   | 14.0  | 24.1  | 24.2  | 24.1  | 26.8  | 22.0  | 23.4  | 24.3  | 24.2  | 24.7   | 25.0   | 23.6   |
| M.C. | 21 ± 1 | 27 ± 1 | 30 ± 1 | 30 ± 3 | 30 ± 2 | 43   | 45 ± 3 | 40   | 48    |        |        |        |
| M.V. | 17 ± 2 | 22 ± 1 | 22 ± 1 | 24 ± 1 | 26 ± 1 | 26 ± 2 | 27 ± 3 | 27 ± 3 | 27 ± 3 | 25 ± 1 | 24 ± 1 | 23 ± 1 |

Table 6 presents the study's results pertaining to heart rates (HR, beats per minute). During each week of the study, except for week one, it can be seen that the heart rates of the control animals (C1-C4 and S1) were higher than those of the implanted animals. Thus the inventive device may reduce heart rate in subjects suffering from heart failure. Put another way, the inventive device provides may enhance the efficiency of the pulmonary system and therefore reduce the frequency with which the heart must beat to satisfy the body's oxygen demands.

TABLE 6

Heart Rate (HR, beats per minute)

|    | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|----|-------|-------|-------|-------|-------|-------|-------|-------|-------|--------|--------|--------|
| C1 |       | 131   | 147   | 127   | 127   | 117   | 123   | 127   | 143   |        |        |        |
| C2 |       | 146   | 192   | 165   | 138   | 156   | 149   |       |       |        |        |        |
| C4 |       | 135   |       |       |       |       |       |       |       |        |        |        |
| S1 |       | 143   | 131   | 124   | 123   |       | 125   | 125   | 130   |        | 133    | 131    |
| V1 |       | 121   | 149   | 151   | 110   | 132   | 137   | 94    | 106   | 91     |        |        |
| V2 |       | 142   | 132   | 120   | 140   | 137   | 144   | 126   | 135   |        |        |        |
| V3 |       | 151   | 107   | 74    | 82    | 111   | 98    | 95    | 107   | 112    | 105    | 96     |
| V4 |       | 187   | 159   | 118   | 130   | 139   | 101   | 72    | 112   | 122    |        | 102    |

TABLE 6-continued

Heart Rate (HR, beats per minute)

|  | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| M.C. |  | 139 ± 3 | 157 ± 18 | 139 ± 13 | 129 ± 5 | 136 ± 20 | 133 ± 8 | 126 ± 1 | 136 ± 6 |  | 133 | 131 |
| M.V. |  | 150 ± 4 | 137 ± 1 | 116 ± 16 | 115 ± 3 | 130 ± 6 |  | 120 ± 12 | 97 ± 11 | 115 ± 7 | 108 ± 9 | 105 | 99 ± 2 |

Table 7 presents the study's results relating to oxygen saturation in the vena cava ($VC\_SO_2$, %). The control animals and the implanted animals had similar $VC\_SO_2$ levels throughout the course of the study, although for both groups the levels were lower than at baseline. It is expected that oxygen saturation in the vena cava is relatively low, because the vessel carries deoxygenated blood from the body to the heart.

TABLE 7

Oxygen Saturation in Vena Cava ($VC\_SO_2$, %)

|  | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| C1 | 90 | 85 | 84 | 85 | 80 | 83 | 80 | 80 | 79 |  |  |  |
| C2 |  | 80 | 81 | 75 | 77 |  | 75 | 78 |  |  |  |  |
| C4 |  | 82 | 77 | 62 |  |  |  |  |  |  |  |  |
| S1 |  |  |  |  |  |  |  |  |  |  |  |  |
| V1 | 94 | 80 | 80 | 81 | 79 | 80 | 68 | 80 | 80 | 80 | 79 | 80 |
| V2 | 98 | 78 | 78 | 70 | 81 | 78 | 73 | 79 | 79 |  |  |  |
| V3 |  | 75 | 74 | 75 | 74 | 71 | 75 | 74 | 79 | 67 | 74 | 78 |
| V4 |  | 73 | 73 | 72 | 67 | 76 | 71 | 76 | 79 | 73 | 74 | 75 |
| M.C. | 90 | 82 ± 1 | 81 ± 2 | 74 ± 6 | 79 ± 1 | 79 ± 4 | 79 ± 1 | 80 | 79 |  |  |  |
| M.V. | 96 ± 1 | 76 ± 2 | 76 ± 2 | 75 ± 2 | 75 ± 3 | 76 ± 2 | 72 ± 1 | 77 ± 2 | 79 ± 0 | 73 ± 4 | 76 ± 2 | 78 ± 1 |

Table 8 presents the study's results relating to oxygen saturation in the pulmonary artery ($PA\_SO_2$, %). The $PA\_SO_2$ values for the implanted animals are somewhat higher than those for the control animals (e.g., between about 5-10% higher), indicating that device 100 was patent and transferring blood from the left atrium to the right atrium. It is expected that oxygen saturation in the pulmonary artery is relatively low, because the vessel carries deoxygenated blood from the heart to the lungs.

TABLE 8

Oxygen Saturation in Pulmonary Artery ($PA\_SO_2$, %)

|  | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| C1 | 84 | 81 | 76 | 78 | 71 |  | 76 | 75 | 73 |  |  |  |
| C2 |  | 64 | 77 | 67 | 70 | 69 | 70 |  |  |  |  |  |
| C4 |  | 78 | 76 | 57 |  |  |  |  |  |  |  |  |
| S1 |  |  |  |  |  |  |  |  |  |  |  |  |
| V1 | 91 | 81 | 83 | 82 | 81 | 85 | 82 | 83 | 84 | 83 | 80 | 80 |
| V2 | 92 | 81 | 80 | 84 | 87 | 87 | 80 | 82 | 84 |  |  |  |
| V3 |  | 77 | 79 | 84 | 79 | 76 | 80 | 78 | 85 | 71 | 77 | 81 |
| V4 |  | 76 | 80 | 84 | 75 | 78 | 76 | 83 | 83 | 78 | 77 | 77 |
| M.C. | 84 | 74 ± 5 | 76 ± 0 | 67 ± 5 | 71 ± 0 | 69 | 73 ± 2 | 75 | 73 |  |  |  |
| M.V. | 92 ± 0 | 79 ± 1 | 81 ± 1 | 84 ± 1 | 81 ± 3 | 82 ± 3 | 80 ± 1 | 81 ± 1 | 84 ± 0 | 77 ± 3 | 78 ± 1 | 79 ± 1 |

Table 9 presents the oxygen saturation in the left atrium ($LA\_SO_2$, %). The $LA\_SO_2$ values for the implanted animals are similar to those for the control animals. Animals with $LA\_SO_2$ values of less than 94% are considered to have low cardiac output.

TABLE 9

Oxygen Saturation in Left Atrium (LA_SO$_2$, %)

|  | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| C1 | 100 | 96 | 97 | 94 | 93 | 95 | 92 | 96 | 93 |  |  |  |
| C2 |  | 96 | 97 | 98 | 99 | 96 | 95 |  |  |  |  |  |
| C4 |  | 95 | 95 | 98 |  |  |  |  |  |  |  |  |
| S1 |  |  |  |  |  |  |  |  |  |  |  |  |
| V1 | 100 | 93 | 96 | 97 | 94 | 96 | 97 | 97 | 97 | 97 | 96 | 96 |
| V2 | 100 | 97 | 97 | 96 | 92 | 96 | 87 | 95 | 97 |  |  |  |
| V3 |  | 96 | 93 | 97 | 96 | 93 | 97 | 96 | 96 | 94 | 96 | 96 |
| V4 |  | 95 | 96 | 96 | 97 | 97 | 97 | 99 | 98 | 97 | 98 | 98 |
| M.C. | 100 | 96 ± 0 | 96 ± 1 | 97 ± 1 | 96 ± 2 | 96 ± 1 | 94 ± 1 | 96 | 93 |  |  |  |
| M.V. | 100 ± 0 | 95 ± 1 | 96 ± 1 | 97 ± 0 | 95 ± 1 | 96 ± 1 | 95 ± 3 | 97 ± 1 | 97 ± 0 | 96 ± 1 | 97 ± 1 | 97 ± 1 |

Table 10 presents the study's results pertaining to the left ventricle internal diameter in diastole (LVIDd, cm), which also may be referred to in the art as left ventricular end-diastolic dimension (LVEDD or LVDD). It may be seen that the LVIDd for the control (C1-C4 and S1) and implanted (V1-V4) animals were relatively similar, and does not significantly vary during weeks 1-12 of the study. This may be attributed to the relatively low pressures during implantation. It may be expected that when the device 100 is implanted in a subject with high LAP, the LVIDd will decrease after implantation as a result of the significant reduction in LAP.

systolic dimension (LVESD or LVSD). While the LVIDd discussed above with respect to Table 10 was similar for both groups of animals, it may be seen here that for the control animals, the LVIDs increased from baseline in week one (e.g., from an average 3.5±0.2 at baseline to 4.2±0.3 at week one), and then increased further and/or remained elevate. By comparison, the LVIDs for the implanted animals increased slightly from baseline in week one (e.g., from an average 4.0±0.2 at baseline to 4.2±0.4 at week one), but then decreased relatively steadily over the course of the study (e.g., to 3.5±0.4 at week twelve). This decrease reflects

TABLE 10

Left Ventricle Internal Diameter in Diastole (LVIDd, cm)

|  | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| C1 | 4.6 | 5.4 | 5.0 | 5.1 | 5.4 | 5.3 | 4.8 | 4.8 | 4.8 |  |  |  |
| C2 | 4.0 | 4.1 | 4.4 | 4.4 | 4.0 | 4.0 | 3.8 |  |  |  |  |  |
| C4 | 4.2 | 5.7 | 5.7 | 5.5 |  |  |  |  |  |  |  |  |
| S1 | 4.3 | 4.7 | 4.9 | 5.0 | 4.7 |  | 5.0 | 5.0 | 5.0 |  | 4.4 | 5.0 |
| V1 | 3.8 | 4.1 | 4.2 | 4.3 | 3.8 | 4.0 | 4.1 | 4.5 | 4.3 | 4.4 | 4.3 | 4.0 |
| V2 | 5.3 | 4.5 | 4.5 | 5.4 | 5.0 | 4.9 | 5.0 | 4.9 | 5.0 |  |  |  |
| V3 | 5.4 | 6.3 | 6.2 | 5.9 | 6.0 | 5.6 | 5.5 | 6.0 | 6.2 | 6.3 | 5.9 | 5.6 |
| V4 | 4.4 | 4.9 | 4.7 | 4.3 | 4.0 | 3.9 | 4.1 | 4.1 | 4.1 | 4.2 | 4.4 | 4.1 |
| M.C. | 4.3 ± .1 | 5.0 ± .4 | 5.0 ± .3 | 5.0 ± .2 | 4.7 ± .4 | 4.7 ± .7 | 4.5 ± .4 | 4.9 ± .1 | 4.9 ± .1 |  | 4.4 | 5.0 |
| M.V. | 4.7 ± .4 | 5.0 ± .5 | 4.9 ± .4 | 5.0 ± .4 | 4.7 ± .5 | 4.6 ± .4 | 4.7 ± .3 | 4.9 ± .4 | 4.9 ± .5 | 5.0 ± .7 | 4.9 ± .5 | 4.6 ± .5 |

Table 11 presents the study's results pertaining to the left ventricle internal diameter in systole (LVIDs, cm), which also may be referred to in the art as left ventricular endthe remodeling of the left ventricle over time that results from offloading blood flow from the left atrium back to the right atrium through the inventive device.

TABLE 11

Left Ventricle Internal Diameter in Systole (LVIDs, cm)

|  | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| C1 | 3.8 | 4.7 | 4.4 | 4.5 | 4.9 | 4.9 | 4.4 | 4.4 | 4.4 |  |  |  |
| C2 | 3.0 | 3.3 | 3.8 | 3.8 | 3.5 | 3.7 | 3.6 |  |  |  |  |  |
| C4 | 3.5 | 4.8 | 5.0 | 5.1 |  |  |  |  |  |  |  |  |
| S1 | 3.6 | 4.1 | 4.3 | 4.4 | 4.2 |  | 4.5 | 4.6 | 4.6 |  | 4.7 | 4.7 |
| V1 | 3.6 | 3.5 | 3.5 | 3.6 | 3.2 | 3.3 | 3.4 | 3.7 | 3.6 | 3.6 | 3.5 | 3.2 |
| V2 | 4.7 | 3.8 | 3.7 | 3.8 | 4.0 | 3.9 | 3.9 | 3.9 | 4.0 |  |  |  |
| V3 | 4.6 | 5.3 | 5.2 | 4.9 | 4.9 | 4.6 | 4.5 | 4.9 | 5.0 | 5.0 | 4.7 | 4.4 |
| V4 | 3.4 | 4.0 | 3.7 | 3.3 | 3.1 | 2.9 | 3.1 | 3.1 | 3.0 | 3.1 | 3.2 | 2.9 |
| M.C. | 3.5 ± .2 | 4.2 ± .3 | 4.3 ± .3 | 4.5 ± .3 | 4.2 ± .4 | 4.3 ± .6 | 4.2 ± .3 | 4.5 ± .1 | 4.5 ± .1 |  | 4.7 | 4.7 |
| M.V. | 4.0 ± .3 | 4.2 ± .4 | 4.0 ± .4 | 3.9 ± .4 | 3.8 ± .4 | 3.7 ± .4 | 3.7 ± .3 | 3.9 ± .4 | 3.9 ± .4 | 3.9 ± .6 | 3.8 ± .5 | 3.5 ± .4 |

Table 12 elaborates on the results of Table 11, and presents the changes in the left ventricle internal diameter in systole (ΔLVIDs, %). As can be seen in Table 12, the control animals experienced an average increase in LVIDs of about 20-29% over the course of the study, while the implanted animals experienced an average decrease in LVIDs of about 0-9%. Thus, the inventive device may inhibit increases in the internal diameter of the left ventricle in subjects suffering from heart disease, and indeed may reduce the internal diameter of the left ventricle in subjects suffering from heart disease, in some embodiments by up to 10%.

TABLE 12

Change in Left Ventricle Internal Diameter in Systole (ΔLVIDs, %)

| | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| C1 | | +23 | +15 | +18 | +28 | +28 | +16 | +16 | +16 | | | |
| C2 | | +11 | +25 | +27 | +17 | +23 | +20 | | | | | |
| C4 | | +37 | +43 | +46 | | | | | | | | |
| S1 | | +13 | +17 | +22 | +17 | | +24 | +26 | +27 | | +29 | +28 |
| V1 | | −1 | −2 | +1 | −11 | −8 | −6 | +4 | +1 | +2 | −2 | −10 |
| V2 | | −18 | −21 | −19 | −14 | −17 | −17 | −17 | −14 | | | |
| V3 | | +17 | +13 | +8 | +7 | +1 | −2 | +7 | +10 | +10 | +2 | −4 |
| V4 | | +19 | +9 | −2 | −9 | −12 | −7 | −8 | −9 | −8 | −6 | −14 |
| M.C. | | +21 ± 6 | +25 ± 6 | +28 ± 6 | +21 ± 4 | 25 ± 2 | +20 ± 2 | +21 ± 5 | +22 ± 6 | | +29 | +28 |
| M.V. | | +4 ± 9 | +0 ± 8 | −3 ± 6 | −7 ± 5 | −9 ± 4 | −8 ± 3 | −4 ± 6 | −3 ± 5 | +1 ± 5 | −2 ± 2 | −9 ± 3 |

Table 13 presents the study's results pertaining to ejection fraction (EF, %). The EF of the control animals may be seen to decline significantly over the course of the study, while the EF of the implanted animals increases significantly over the course of the study. For example, it may be seen that for the control animals, C1 experienced a decline in EF to about 45% of baseline; C2 to about 28% of baseline; C4 to about 47% of baseline; and S1 to about 41% of baseline. By comparison, for the implanted animals, V1 experienced an increase in EF to about 169% of baseline; V2 also to about 169% of baseline; V3 to about 129% of baseline; and V4 to about 127% of baseline. The inventive device thus may not only inhibit decreases in EF of subjects suffering from heart failure, but indeed may increase the EF of such subjects significantly, for example by 25-50%, or even 25-70% or more.

Table 14 elaborates on the results presented in Table 14, and presents the change in ejection fraction. As can be seen in Table 14, the EF of each of the control animals decreased significantly relative to baseline, e.g., by up to 72% for animal C2, while the EF for each of the implanted animals increased significantly.

As noted above with respect to Table 10, the left ventricle internal diameter in diastole (LVIDd) did not significantly change for the implanted animals over the course of the study. Absent such a decrease in the LVIDd, an increase in the EF may be interpreted as an increase in cardiac output. The inventive device thus may not only inhibit decreases in cardiac output of subjects suffering from heart failure, but indeed may increase the cardiac output of such subjects significantly.

TABLE 13

Ejection Fraction (EF, %)

| | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| C1 | 35.5 | 28.9 | 26.8 | 23.5 | 21.0 | 18.3 | 17.8 | 16.4 | 16.0 | | | |
| C2 | 45.3 | 40.1 | 29.1 | 28.0 | 23.6 | 20.9 | 12.7 | | | | | |
| C4 | 34.3 | 32.4 | 25.2 | 16.2 | | | | | | | | |
| S1 | 33.2 | 27.6 | 26.9 | 25.0 | 22.6 | | 20.7 | 18.6 | 16.8 | | 14.8 | 13.7 |
| V1 | 24.5 | 27.3 | 36.1 | 36.6 | 35.9 | 36.0 | 35.7 | 35.7 | 35.6 | 37.7 | 37.8 | 41.4 |
| V2 | 26.4 | 33.2 | 37.3 | 37.2 | 40.5 | 42.0 | 42.9 | 43.0 | 44.6 | | | |
| V3 | 32.6 | 33.6 | 33.3 | 34.5 | 37.2 | 37.2 | 37.9 | 38.2 | 38.9 | 41.0 | 41.8 | 41.9 |
| V4 | 45.3 | 45.7 | 46.0 | 47.5 | 47.9 | 47.8 | 47.9 | 49.7 | 52.7 | 53.2 | 55.5 | 57.5 |
| M.C. | 37.1 ± 2.8 | 32.3 ± 2.8 | 27.0 ± .8 | 23.2 ± 2.5 | 22.4 ± .7 | 19.6 ± 1.3 | 17.0 ± 2.3 | 17.5 ± 1.1 | 16.4 ± .4 | | 14.8 | 13.7 |
| M.V. | 32.2 ± 4.7 | 34.9 ± 3.9 | 38.2 ± 2.7 | 39.0 ± 2.9 | 40.4 ± 2.7 | 40.8 ± 2.7 | 41.1 ± 2.7 | 41.6 ± 3.1 | 42.9 ± 3.7 | 44.0 ± 4.7 | 45.0 ± 5.4 | 46.9 ± 5.3 |

TABLE 14

Change in Ejection Fraction (EF, %)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   |       | −18   | −24   | −34   | −41   | −48   | −50   | −54   | −55   |        |        |        |
| C2   |       | −11   | −36   | −38   | −48   | −54   | −72   |       |       |        |        |        |
| C4   |       | −6    | −19   | −53   |       |       |       |       |       |        |        |        |
| S1   |       | −17   | −27   | −25   | −32   |       | −38   | −44   | −49   |        | −55    | −59    |
| V1   |       | +11   | +47   | +49   | +46   | +47   | +46   | +45   | +45   | +54    | +54    | +69    |
| V2   |       | +26   | +42   | +41   | +54   | +59   | +63   | +63   | +69   |        |        |        |
| V3   |       | +3    | +2    | +6    | +14   | +14   | +16   | +17   | +19   | +26    | +28    | +29    |
| V4   |       | +1    | +2    | +5    | +6    | +6    | +6    | +10   | +16   | +18    | +23    | +27    |
| M.C. |       | −13 ± 3 | −26 ± 4 | −37 ± 6 | −40 ± 5 | −51 ± 3 | −53 ± 10 | −49 ± 5 | −52 ± 3 |        | −55    | −59    |
| M.V. |       | +10 ± 6 | +23 ± 2 | +25 ± 12 | +30 ± 12 | +32 ± 13 | +33 ± 13 | +34 ± 12 | +38 ± 12 | +32 ± 11 | +35 ± 10 | +41 ± 14 |

Table 15 presents the study's results pertaining to fractional shortening (FS, %). Similar to ejection fraction discussed above with respect to Tables 13-14, the FS of each of the control animals may be seen in Table 15 to decline significantly over the course of the study. For example, animal C1 experienced a decline in FS to about 47% of baseline before death; animal C2 to about 24% of baseline; animal C4 to about 46% of baseline; and animal S1 to about 39% of baseline. In contrast, the FS of each of the implanted animals increased significantly over the course of the study. For example, animal V1 experienced an increase in FS to about 183% of baseline; animal V2 to about 166% of baseline; animal V3 to about 132% of baseline; and animal V4 to about 127% of baseline. Thus, the inventive device not only inhibits decreases in fractional shortening for subjects suffering from heart failure, but also may increase fractional shortening significantly, e.g., by about 25-85% of baseline.

any physical activity without discomfort, exhibit symptoms of cardiac insufficiency at rest, and have increased discomfort if they undertake any physical activity. The present devices may significantly increase the cardiac output of such class III or class IV subjects, particularly those with low ejection fraction, enabling them to engage in significantly more physical activity than they otherwise could. The present devices further may decrease pulmonary artery pressure in subjects with left heart failure, and additionally may reduce or inhibit pulmonary congestion in patients with pulmonary congestion resulting from such heart failure, for example by inhibiting episodes of acute pulmonary edema. Indeed, as the above-described Example illustrates, the inventive device may reduce LAP and PAP significantly relative to what those pressures would otherwise be; such pressure reductions may not only provide immediate relief from acute symptoms, but further may facilitate cardiac

TABLE 15

Fractional Shortening (FS, %)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   | 17.0  | 13.7  | 12.5  | 10.9  | 9.7   | 8.4   | 8.0   | 7.5   | 8.0   |        |        |        |
| C2   | 23.2  | 19.3  | 13.5  | 13.0  | 10.7  | 9.1   | 5.5   |       |       |        |        |        |
| C4   | 16.2  | 15.5  | 11.8  | 7.4   |       |       |       |       |       |        |        |        |
| S1   | 15.6  | 12.8  | 12.5  | 11.6  | 10.3  |       | 9.4   | 8.4   | 7.6   |        | 6.6    | 6.1    |
| V1   | 10.9  | 12.6  | 17.1  | 17.5  | 16.9  | 16.9  | 16.9  | 17.0  | 16.9  | 18.1   | 17.6   | 20.0   |
| V2   | 12.4  | 15.8  | 18.1  | 19.0  | 19.9  | 20.7  | 21.2  | 21.6  | 20.6  |        |        |        |
| V3   | 15.7  | 16.4  | 16.2  | 16.7  | 18.3  | 18.2  | 18.5  | 18.8  | 19.3  | 20.5   | 20.8   | 20.8   |
| V4   | 22.4  | 22.6  | 22.9  | 23.7  | 23.7  | 23.6  | 23.8  | 24.9  | 26.7  | 27.1   | 28.8   | 28.4   |
| M.C. | 18.0 ± 1.8 | 15.3 ± 1.4 | 12.6 ± 0.4 | 10.7 ± 1.2 | 10.2 ± 0.3 | 8.7 ± 0.4 | 7.7 ± 1.2 | 8.0 ± 0.4 | 7.8 ± 0.2 |        | 6.6    | 6.1    |
| M.V. | 15.3 ± 2.5 | 16.8 ± 2.1 | 18.6 ± 1.5 | 19.2 ± 1.6 | 19.7 ± 1.5 | 19.8 ± 1.5 | 20.1 ± 1.5 | 20.6 ± 1.7 | 20.9 ± 2.1 | 21.9 ± 2.7 | 22.4 ± 3.3 | 23.1 ± 2.7 |

As the foregoing results illustrate, devices constructed and implanted according to the present invention may provide for significantly improved mortality rates in subjects suffering from heart failure. In particular, the devices may significantly enhance ejection fraction, fractional shortening, and/or cardiac output in subjects who would otherwise have significantly diminished cardiac function as a result of excessive left atrial and left ventricular pressures. For example, subjects may be classified under the New York Heart Association (NYHA) classification system as having Class II (Mild) heart failure, who have slight limitation of physical activity and are comfortable at rest, but for whom ordinary physical activity results in fatigue, palpitation, or dyspnea; Class III (Moderate) heart failure, who have marked limitation of physical activity, may be comfortable at rest, and may experience fatigue, palpitation, or dyspnea if they engage in less than normal activity; or as having Class IV (Severe) heart failure, who are unable to carry out remodeling over the weeks following implant and thus provide for enhanced cardiac function. The devices may in some embodiments include means for measuring the various parameters of interest, e.g., means such as discussed above with respect to the animal trials.

It should be noted that the inventive devices also may be used with patients having disorders other than heart failure. For example, in one embodiment the device may be implanted in a subject suffering from myocardial infarction, for example in the period immediately following myocardial infarction (e.g., within a few days of the event, or within two weeks of the event, or even within six months of the event). During such a period, the heart remodels to compensate for reduced myocardial function. For some subjects suffering from severe myocardial infarction, such remodeling may cause the function of the left ventricle to significantly deteriorate, which may lead to development of heart failure. Implanting an inventive device during the period immediately following myocardial infarction may inhibit such deterioration in the left ventricle by reducing LAP and LVEDP during the remodeling period. For example, in the above-described Example, heart failure was induced in the sheep by injecting microspheres that block the coronary artery and induce myocardial infarction. Following the myocardial infarction, the sheep developed heart failure. As can be seen in the various results for the implanted animals, implanting the inventive device even a week following the myocardial infarction inhibited degradation of the heart and yielded significantly improved mortality rates and cardiac functioning both immediately and over time as the subjects' hearts remodeled. As such, it is believed that implanting an inventive device for even a few weeks or months following myocardial infarction may provide significant benefits to the subject as their heart remodels. The device optionally then may be removed.

While various illustrative embodiments of the invention are described above, it will be apparent to one skilled in the art that various changes and modifications may be made herein without departing from the invention. It will further be appreciated that the devices described herein may be implanted in other positions in the heart. For example, device 100 illustrated in FIGS. 1A-1D may be implanted in an orientation opposite to that shown in FIG. 2B, so as to shunt blood from the right atrium to the left atrium, thus decreasing right atrial pressure; such a feature may be useful for treating a high right atrial pressure that occurs in pulmonary hypertension. Similarly, device 100 may be implanted across the ventricular septum, in an orientation suitable to shunt blood from the left ventricle to the right ventricle, or in an orientation suitable to shunt blood from the right ventricle to the left ventricle. The appended claims are intended to cover all such changes and modifications that fall within the true spirit and scope of the invention.

What is claimed:

1. A device for regulating blood pressure between a patient's left atrium and right atrium, the device comprising:
   a stent comprising a neck region and first and second flared end regions, the neck region disposed between the first and second end regions and configured to engage the patient's atrial septum;
   a biocompatible material disposed on the stent in the neck region and the second flared end region, but not on a first portion of the first flared end region; and
   an opening within the stent configured to shunt blood from the left atrium to the right atrium when blood pressure in the left atrium exceeds blood pressure in the right atrium, the opening having an outlet at the first flared end region and an inlet at an edge of the biocompatible material, the biocompatible material adapted to inhibit excessive tissue ingrowth into the opening and channel blood flow through the opening.

2. The device of claim 1, wherein the biocompatible material promotes limited tissue ingrowth into the opening, the tissue ingrowth comprising an endothelial layer inhibiting thrombogenicity of the device.

3. The device of claim 1, wherein an outlet edge of the biocompatible material is about 1-3 mm from a narrowest portion of the neck region.

4. The device of claim 1, wherein the biocompatible material is adapted to smoothly channel blood flow from the left atrium to the right atrium through the opening without high shear rates, stagnation points, or turbulence, and wherein the biocompatible material is adapted to promote ingrowth of a neointima layer to a thickness of less than 0.2 mm so as to render the material inert and inhibit hyperplasia.

5. The device of claim 1, further comprising leaflets disposed completely in the first flared end region and configured to be continuously flushed by blood circulating in the right atrium so as to inhibit excessive tissue ingrowth, stiffening of the leaflets, and impairment of leaflet closure.

6. A method of treating a subject with heart pathology, the subject having a heart with an atrial septum between a right atrium and a left atrium, the method comprising:
   providing a device having first and second flared end regions and a neck region disposed therebetween, an opening within the device, and a biocompatible material disposed on the device in the neck region and the second flared end region, but not on a first portion of the first flared end region;
   deploying the device across a puncture through the atrial septum such that the neck region is positioned in the puncture, the first flared end region is disposed in the right atrium, and the second flared end region is disposed in the left atrium; and
   reducing left atrial pressure and left ventricular end diastolic pressure by shunting blood from the left atrium to the right atrium through the device when the left atrial pressure exceeds the right atrial pressure.

7. The method of claim 6, further comprising identifying a middle of a fossa ovalis of the atrial septum by pressing a needle against the fossa ovalis to partially tent the fossa ovalis, and puncturing the middle of the fossa ovalis with the needle.

8. The method of claim 6, wherein the puncture is through a middle of a fossa ovalis of the atrial septum and the device is deployed away from the limbus, atrial wall, and the ridge between the inferior vena cava and coronary sinus.

9. The method of claim 6, wherein the heart pathology comprises heart failure, pulmonary congestion, pulmonary hypertension, or myocardial infarction, or any combination thereof.

10. The method of claim 9, comprising deploying the device during a period immediately following the myocardial infarction.

11. The method of claim 10, wherein the period immediately following the myocardial infarction is at least two weeks after the myocardial infarction.

12. The method of claim 6, wherein shunting blood from the left atrium to the right atrium increases the cardiac output of the subject, decreases pulmonary congestion of the subject, or decreases the pulmonary artery pressure of the subject, or any combination thereof.

13. The method of claim 6, wherein shunting blood from the left atrium to the right atrium increases the ejection fraction of the subject or increases the fractional shortening of the subject or both.

14. The method of claim 6, wherein shunting blood from the left atrium to the right atrium decreases the left ventricle internal diameter in systole of the subject.

15. The method of claim 6, wherein deploying the device across the puncture comprises deploying the second flared end region by advancing the second flared end region out of a sheath and into the left atrium with a pusher, then partially retracting the sheath such that the second flared end region engages the left side of the atrial septum, and then deploying the first flared end region by fully retracting the sheath such that the first flared end region deploys in the right atrium.

16. The method of claim 15, wherein the pusher is configured to advance only the second flared end region out of the sheath.

17. The method of claim 6, further comprising:
prior to providing the device:
providing a tube of shape-memory metal;
expanding the tube on a mandrel to define the first and second flared end regions and the neck region therebetween, and heating the expanded tube to set the shape; and
coating the neck region and the second flared end region, but not the first portion of the first flared end region, with the biocompatible material.

18. The method of claim 17, wherein the biocompatible material comprises expanded-polytetrafluoroethylene, polyurethane, DACRON (polyethylene terephthalate), silicone, polycarbonate urethane, or pericardial tissue from an equine, bovine, or porcine source.

19. The method of claim 17, further comprising securing leaflets to an outlet edge of the biocompatible material at a portion of the first flared end region that is about 1-3 mm from a narrowest portion of the neck region.

20. The method of claim 17, wherein the device comprises a plurality of sinusoidal rings and longitudinally extending struts, further comprising a valve sutured to the longitudinally extending struts and to the biocompatible material, the valve comprising leaflets.

21. The device of claim 1, wherein the first and second flared end regions each flare by about 50 to 120 degrees.

22. The device of claim 1, wherein the stent comprises a plurality of sinusoidal rings interconnected by longitudinally extending struts.

23. The device of claim 1, wherein the stent comprises a shape memory material.

24. The device of claim 23, wherein the shape memory material comprises a shape memory metal.

25. The device of claim 1, wherein the device is configured so that, when the shunt is deployed across the patient's atrial septum, the first flared end region protrudes 5.5 to 7.5 mm into the right atrium.

26. The device of claim 25, wherein the device is configured so that, when the shunt is deployed across the patient's atrial septum, the second flared end region protrudes 2.5 to 7 mm into the left atrium.

27. The device of claim 1, wherein the neck region has a diameter of 3 to 6 mm.

28. The device of claim 27, wherein the first flared end region has a diameter between 9 and 13 mm and the second flared end region has a diameter between 8 and 15 mm.

29. The device of claim 1, wherein the stent is configured to transition between a collapsed state suitable for percutaneous delivery and an expanded state when deployed across the patient's atrial septum.

30. The device of claim 29, wherein the stent has an hourglass configuration in the expanded state.

31. The device of claim 1, wherein the biocompatible material comprises expanded-polytetrafluoroethylene.

32. The device of claim 1, wherein an opposing edge of the biocompatible material is at least partially before a distal end of the first flared end region.

33. The device of claim 1, wherein the first and second flared end regions each flare outwardly away from the atrial septum.

34. The device of claim 1, wherein respective distal ends of each of the first and second flared end regions do not contact the atrial septum when the device is deployed.

* * * * *

UNITED STATES PATENT AND TRADEMARK OFFICE
CERTIFICATE OF CORRECTION

PATENT NO. : 9,980,815 B2  
APPLICATION NO. : 14/712801  
DATED : May 29, 2018  
INVENTOR(S) : Yaacov Nitzan and Menashe Yacoby Page 1 of 1

It is certified that error appears in the above-identified patent and that said Letters Patent is hereby corrected as shown below:

On the second page, under the Related U.S. Application Data item (60), Line 11, after "61/425,792, filed on":
Delete "May 4, 2010" and Insert --Dec. 22, 2010--

Signed and Sealed this  
Third Day of July, 2018

Andrei Iancu  
*Director of the United States Patent and Trademark Office*